United States Patent
Deleuze-Masquefa et al.

(10) Patent No.: US 8,378,098 B2
(45) Date of Patent: Feb. 19, 2013

(54) IMIDAZOL[1,2-α]QUINOXALINES AND DERIVATIVES FOR THE TREATMENT OF CANCERS

(75) Inventors: Carine Deleuze-Masquefa, Saint Jean de Vedas (FR); Georges Moarbess, Nord (LY); Pierre-Antoine Bonnet, Montpellier (FR); Frédéric Pinguet, Montarnaud (FR); Ali Bazarbachi, Beirut (LY); Françoise Bressolle, Montpellier (FR)

(73) Assignees: Universite de Montpellier I, Montpellier (FR); American University of Beirut, Beirut (LB); Centre Regional de Lutte Contre le Cancer de Montpellier, Montpellier (FR)

( * ) Notice: Subject to any disclaimer, the term of this patent is extended or adjusted under 35 U.S.C. 154(b) by 155 days.

(21) Appl. No.: 12/681,201

(22) PCT Filed: Oct. 3, 2008

(86) PCT No.: PCT/EP2008/063290
§ 371 (c)(1), (2), (4) Date: Apr. 1, 2010

(87) PCT Pub. No.: WO2009/043934
PCT Pub. Date: Apr. 9, 2009

(65) Prior Publication Data
US 2010/0249142 A1   Sep. 30, 2010

(30) Foreign Application Priority Data

Oct. 3, 2007 (FR) .................................... 07/06928

(51) Int. Cl.
*C07D 471/00* (2006.01)
(52) U.S. Cl. ..................................................... 544/346
(58) Field of Classification Search ............... 544/346
See application file for complete search history.

(56) References Cited

FOREIGN PATENT DOCUMENTS

| CA | 2158167 | * 10/1994 |
|---|---|---|
| WO | 93/04066 | 3/1993 |
| WO | 2007/087250 | 8/2007 |
| WO | 2007/109813 | 9/2007 |

OTHER PUBLICATIONS

Zurbonsen et al.; "Antiproliferative Effects of Imidazo[1,2-a]Pyrazine Derivatives on the Dami Cell Line"; Biochemical Pharmacology, Vol. 54, pp. 365-371, 1997.

Catarzi et al.; "Structure-Activity Relationship of 1,2,4-Triazolo[1,5-a]Quinoxalines and Their 1-Deaza Analogues Imidazo[1,2-a]Quinoxalines at the Benzodiazepine Receptor"; J. Med. Chem. 1994, 37, 2846-2850.

Colotta et al.; "Synthesis of Some Tricyclic Heteroaromatic Systems and Their A1 and A2a Adenosine Binding Activity"; Eur. J. Med. Chem. (1995) 30, 133-139.

Corona et al.; "4-Substituted Anilino Imidazo[1,2-a] and Triazolo[4,3-a]Quinoxalines. Synthesis and Evaluation of in Vitro Biological Activity"; European Journal of Medicinal Chemistry 41 (2006) 1102-1107.

Deleuze-Masquefa et al.; "Design and Synthesis of Novel Imidazo[1,2-a]Quinoxalines As PDE4 Inhibitors"; Bioorganic & Medicinal Chemistry 12 (2004) 1129-1139.

Morjaria et al.; "Impairment of TNF-a Production and Action by Imidazo[1,2-a]Quinoxalines, A Derivative Family Which Displays Potential Anti-Inflammatory Properties"; International Journal of Immunopathology and Pharmacology; Vol. 19, No. 3. 525-538 (2006).

Zurbonsen et al.; "Apoptotic Effects of Imidazo[1,2-a]Pyrazine Derivatives in the Human Dami Cell Line"; European Journal of Pharmacology 320 (1997) 215-221.

International Search Report based on PCT/EP2008/063920 dated Dec. 15, 2008.

Morjaria et al.; "Impairment of TNF-α Production and Action by Imidazo[1,2- a] Quinoxalines, A Derivative Family Which Displays Potential Anti-Inflammatory Properties"; International Journal of Immunopathology and Pharmacology; Vol. 19, No. 3, p. 525-538; 2006.

Bonnard et al.; "Synthesis and Evaluation of in Vitro Antitumoral Activity of Imidazo [1,2-α] Quinoxaline and Imidazo[1,5-α]Quinoxaline Derivatives"; RICT; 2005.

* cited by examiner

*Primary Examiner* — Douglas M Willis
(74) *Attorney, Agent, or Firm* — Baker Donelson Bearman Caldwell & Berkowitz, PC

(57) ABSTRACT

Imidazo[1,2-a]quinoxaline compounds for the treatment of cancers as well as pharmaceutical compositions that include these compounds and their uses in therapy.
The compound of general formula (I):

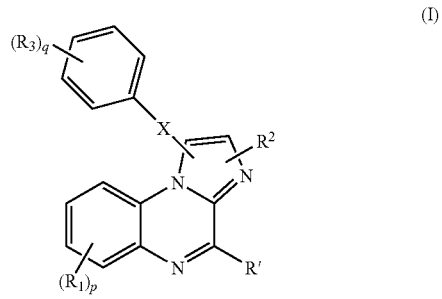

10 Claims, 3 Drawing Sheets

IMIDAZOL[1,2-α]QUINOXALINES AND DERIVATIVES FOR THE TREATMENT OF CANCERS

CROSS REFERENCE TO RELATED APPLICATIONS

This application is a §371 National Stage Application of PCT/EP2008/063290 filed Oct. 3, 2008, which claims priority to French Application 07/06928 filed Oct. 3, 2007.

BACKGROUND OF THE INVENTION

Field of the Invention

The present invention relates to imidazo[1,2-a]quinoxaline compounds for the treatment of cancers as well as pharmaceutical compositions that include these compounds and their uses in therapy. The invention also relates to the use of compounds derived from imidazo[1,2-a]quinoxaline for the preparation of drugs for the treatment of cancers and in particular for the treatment of melanomas and T-cell lymphomas.

Description of Related Art

Given the relative ineffectiveness of a great majority of traditional anti-cancer drugs in the treatment of cancers such as prostate cancers, colon cancers, breast cancers, melanomas, and lymphomas, research is directed towards new therapeutic strategies. Indeed, to succeed in circumventing the problems of resistances and metastases, encountered more and more often in this type of disease, represents an important challenge for research.

Melanoma

Responsible for several thousand deaths each year in France, skin cancer is one of the most dreadful cancers. Its frequency increases very strongly with age, the reduction in ozone and a high exposure to the sun. Taking into account ever-increasing life expectancy and increases in its frequency, skin cancer soon will be one of the most significant public health problems. Melanoma, which resembles a simple mole or beauty spot, is the most serious skin cancer. A melanoma can be benign (nevus) or malignant (malignant melanoma or melanoblastoma). Although malignant melanomas account for only 10% of skin cancers, they are deadly if not treated. It is one of the most aggressive cancers that exist, but treatment at an early stage makes it possible to cure the patient. An untreated malignant melanoma quickly invades the skin and progresses towards the rest of the body, particularly the liver, lungs, bones and brain, resulting in the death of the patient in a few months.

Adult T-Cell Leukaemia Related to HTLV-1

HTLV-1 (human T-cell lymphotropic virus type 1), discovered in 1980, is the first oncogenic retrovirus discovered in man. Adult T-cell leukaemia, or ATL, is a malignant lymphoid proliferation, bearing T lymphocytes, generally CD4+. These T lymphocytes express on their surface T lymphocyte markers CD2, CD3, CD4, CD5, CD45RO, but do not express marker CD7 and seldom CD8. ATL cells are characterized by the presence of provirus HTLV-I integrated in a monoclonal fashion, rarely in an oligoclonal fashion.

The diversity of the clinical presentation and the highly variable evolution according to the mode of presentation has justified their classification in four clinical forms which can follow one another:

The acute form of ATL (>5%). This pathology, which occurs in the adult, has a very gloomy prognosis with resistance or early relapse even after intensive polychemotherapies. The median of survival is about 6 months.

The chronic form of ATL has a slower evolution, with less severe clinical signs. It presents a lymphocytosis with a high number of leukaemic cells (>5).

A less severe form: subacute ATL, also called smouldering, characterized by a progressive evolution over a long period, with the presence of a few leukaemic cells in the circulating blood (1-5%).

A lymphomatous form is characterized by a low level of leukaemic cells in the circulating blood (<1%). Like the acute form, it has a very grim prognosis.

Peripheral T-Cell Lymphomas

Peripheral T-cell lymphomas account for approximately 15% of all non-Hodgkin's lymphomas. These T-lymphomas have a relatively severe prognosis, with a complete remission rate clearly lower than that of B lymphomas, and a significantly higher relapse rate. Moreover, these T-lymphomas have not profited from the therapeutic progress in B-lymphomas due to the use of rituximab, anti-CD20 monoclonal antibody.

Great hopes were placed in immunotherapy, which contrary to other therapies makes it possible to treat the body as a whole and can eliminate tumour cells disseminated throughout the body. Among the various immunotherapy approaches, the discovery of imiquimod (Aldara®), the first anti-cancer immunomodulator, effective in particular against certain cancers of the skin such as melanoma, was a step forward on this new pathway. Imiquimod is a nitrogenised tricyclic molecule, of the imidazoquinoline family (WO 2006/070408, U.S. Pat. No. 4,689,338). It is primarily known for its antiviral activity against certain viruses such as herpes simplex II, Sendai virus and papilloma virus. The latest publications on this molecule also demonstrate a significant immunomodulating antitumor activity on cancers of the skin, such as basocellular carcinomas, actinic keratoses and melanomas. More recent studies also showed effectiveness against cutaneous metastases and vascular tumours. Imiquimod is thus the first of a new class of anti-cancer drugs called innate and acquired immune response modifiers whose mechanism of action differs from all known anti-cancer drugs such as nitrogen mustards, nitroso-ureas, alkylating agents, organoplatinums, etc.

Deleuze-Masquefa et al. (Biorganic & Medicinal Chemistry 12: 1129-1139, 2004) described imidazo[1,2-a]quinoxaline derivatives as PDE4 (phosphodiesterase 4) inhibitors. In contrast with imiquimod, these molecules inhibit the production and the effects of TNF-α in vitro and thus they seem to have a mode of action different from imiquimod. These derivatives may be of interest for their anti-inflammatory properties (Mojaria et al. International Journal of Immunopathology and Pharmacology, Vol. 19, no. 2, 77-90, 2006).

Anti-cancer activity, and a fortiori activity on melanomas or lymphomas, is neither described nor suggested in these documents.

Bonnard et al. (RICT 2005, Paris) described the synthesis and the evaluation for their antitumor activity of imidazo[1,2-a]quinoxaline derivatives. The structure of the compounds tested is, however, not described.

US 2003/0022898 described derivatives also having an anti-inflammatory activity including compound 4-(2'-aminoethyl)-amino-1,8-dimethylimidazo(1,2-a)quinoxaline. This compound is also described as having an anti-melanoma activity in document US 2006/0025419.

Colotta et al. (Eur. J. Med. Chem., 30, 133-139, 1995) described various compounds including imidazo[1,2-a]quinoxalines. Triazoloquinoxalines are described as binding to the adenosine receptor. Particular applications of imidazo[1,2-a]quinoxalines are not described.

Catarzi et al. (J. Med. Chem., 37, 2846-2850, 1994) described triazoloquinoxalines as well as imidazoquinoxalines binding to the benzodiazepine receptor. Molecules binding to the benzodiazepine receptor are in general recognized for their anxiolytic activities. This document does not describe applications to cancer.

WO 93/04066 described imidazoquinoxalinol compounds binding specifically to GABAa receptors. Only therapeutic uses as sedatives, anxiolytics, anticonvulsives, etc., are considered. Applications in other therapeutic fields and in particular for the treatment of cancers are neither described nor suggested by this document.

Zurbonsen et al. (European Journal of Pharmacology, 320, 215-221, 1997 and Biochemical Pharmacology, 54, 365-371, 1997) describe imidazo[1,2-a]pyrazine derivatives that have an inhibiting activity on phosphodiesterases and are able to induce the apoptosis of a leukaemic cell line. It should be noted, however, that all phosphodiesterase inhibitors do not exhibit anti-cancer activity. Moreover, the compounds of the present invention are distinguished by high activity demonstrated in in vitro and in vivo tests as well on lymphoma as on melanoma.

WO 2007/109813 relates to imidazoquinoxalines having immunomodulator activity. Only applications in the field of adjuvants and vaccines are described. This document envisages potential applications in many therapeutic fields including cancer but no in vitro or in vivo data confirms any anti-cancer activity.

WO 2007/087250 describes 5-LO (lipoxygenase) inhibitors. Applications in the field of cancer are not described.

SUMMARY OF THE INVENTION

To remedy the disadvantages of the state of the art, the present invention proposes imidazo[1,2-a]quinoxaline derivative compounds for the treatment of cancers and more particularly melanomas and lymphomas with T-cells. These compounds can be used for the preparation of drugs for the treatment of cancers.

Advantageously, the compounds of the present invention exhibit improved effectiveness as well as low toxicity. The compounds of the present invention have for example improved effectiveness compared to imiquimod.

Moreover, the compounds of the present invention have shown activity on melanoma but also on lymphoma in in vitro and in vivo tests.

Advantageously, the compounds of the present invention do not have pro-inflammatory activity in contrast to other molecules used in the treatment of cancers such as imiquimod.

DETAILED DESCRIPTION OF A PREFERRED EMBODIMENT

Figure 1:
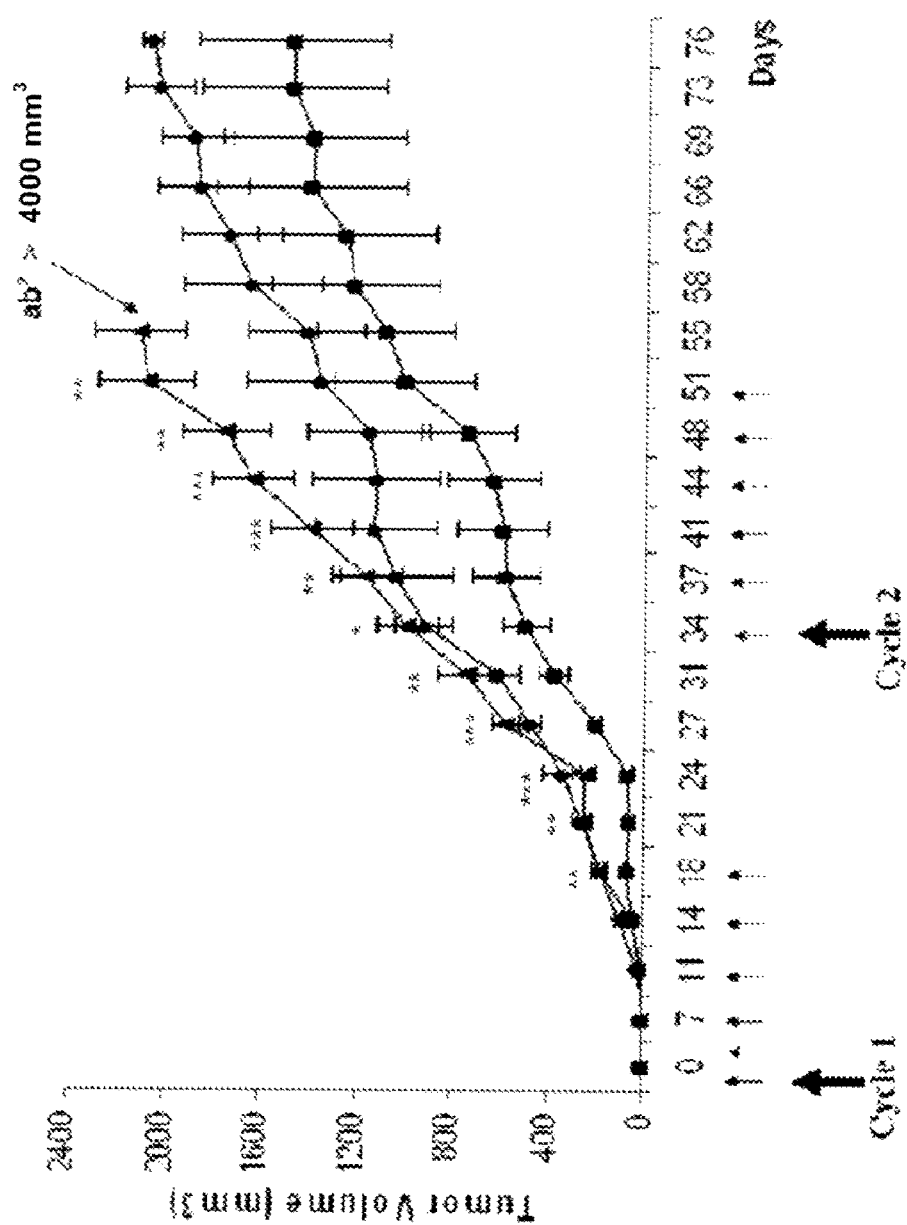
FIGS. 1-3 represent embodiments as described herein.

The invention relates to compounds of general formula (I):

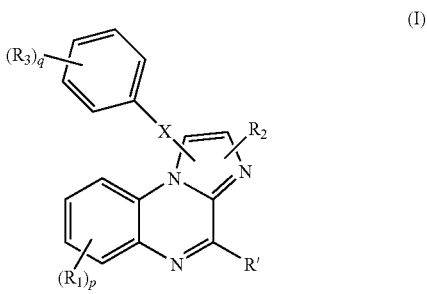

wherein
$R_1$, $R_2$, $R_3$ and R' represent independently an atom of hydrogen, a halogen or a group chosen among the hydroxy, alkyl, alkenyl, cycloalkyl, thioalkyl, alkoxy, amino, alkylamino, dialkylamino, acyl, aryl, aralkyl groups or a saturated or non-saturated heterocycle, optionally substituted by one or more substituents, and the cyano, nitroso, nitro, $-CF_3$, $-(CH_2)_n NR_4 R_5$, $-(CH_2)_n COR_4$, $-(CH_2)_n CO-NR_4 R_5$, $-(CH_2)_n SO_2 -NH_4 R_5$, $-(CH_2)_n CO_2 R_4$, $-NH-(CH_2)_n NR_4 R_5$ radicals,
n ranging between 0 and 4,
p ranging between 1 and 4,
q ranging between 1 and 5,
X representing $(CH_2)_m$, $(CH_2)_m O(CH_2)_{m'}$, $(CH_2)_m NH(CH_2)_{m'}$,
m ranging between 0 and 4,
m' ranging between 0 and 4,
$R_4$ and $R_5$ represent independently an atom of hydrogen or group chosen among the linear or branched $C_1$-$C_4$ alkyl, linear or branched $C_1$-$C_4$ alkenyl, $C_3$-$C_7$ cycloalkyl, acyl, aryl, aralkyl radicals or a heterocycle, optionally substituted by one or more substituents,
and physiologically acceptable salts of same.

Preferentially, $R_1$, $R_2$, $R_3$, and R' represent independently an atom of hydrogen, a halogen or a group chosen among the hydroxyl, $C_1$ to $C_4$ alkyl, $C_2$ to $C_4$ alkenyl, $C_1$ to $C_4$ thioalkyl, $C_1$ to $C_4$ alkoxy, amino, $C_1$ to $C_4$ alkylamino, $C_1$ to $C_4$ dialkylamino, $C_1$ to $C_4$ acyl, $C_1$ to $C_4$ aryl, $C_1$ to $C_4$ aralkyl groups, optionally substituted by one or more substituents, and the cyano, nitroso, nitro, $-CF_3$, $(CH_2)_n NR_4 R_5$, $-(CH_2)_n COR_4$, $-(CH_2)_n CO-NR_4 R_5$, $-(CH_2)_n SO_2-NR_4 R_5$, $-(CH_2)_n CO_2 R_4$, $-NH-(CH_2)_n NR_4 R_5$ radicals,
n ranging between 0 and 4,
p ranging between 1 and 4,
q ranging between 1 and 5.
$R_4$ and $R_5$ represent independently an atom of hydrogen or a group chosen among linear or branched $C_1$-$C_4$ alkyl, linear or branched $C_1$-$C_4$ alkenyl, $C_3$-$C_7$ cycloalkyl radicals.

Preferably, $R_1$, $R_2$ and $R_3$ represent independently an atom of hydrogen, a halogen or a group chosen among the groups methyl, ethyl, propyl, isopropyl, butyl, isobutyl, tertiobutyl, and —$(CH_2)_{n''}$—$(CH=CH)$—$(CH_2)_{n'''}$—$CH_3$ with n" and n''' independently between 0 and 4, $COOR_4$, $NR_4R_5$ and $OR_4$, $R_4$ and $R_5$ are defined above.

R' represents independently an atom of hydrogen, a halogen or a group chosen among the hydroxy, alkoxy, amino, alkylamino, dialkylamino groups, a saturated or non-saturated heterocycle or and —NH—$(CH_2)_n NR_4R_5$.

Preferentially, $R_1$ is hydrogen.

Preferentially, $R_2$ is hydrogen.

Preferentially, $R_3$ is selected among H, Cl, Br, F, hydroxy, methyl, methoxy, ethoxy, $CF_3$, CN, COOH, $COOCH_3$, $COOCH_2CH_3$, $COONH_2$, CHO, $NO_2$ and $C_4H_3O$. More preferentially, $R_3$ is selected among H, hydroxy, methoxy, ethoxy, Br, $CF_3$, Cl and COOH.

Preferably, X is selected among O, NH, $CH_2$, $(CH_2)_2$, $O(CH_2)_{m'}$, and $NH(CH_2)_{m'}$, with m' defined above. Preferentially, X is $(CH2)_2$.

Preferably, R' is a chloro, methoxy, amino, methylamino, dimethylamino, ethylamino, diethylamino, aminomethylamine or aminoethylamine group. Preferentially, R' is —NH—$CH_3$, —$NH_2$ or —NH—$(CH_2)_2$—$NH_2$.

Preferably, q=1 or 2. Preferentially, q=1.

Preferentially, q=1 and $R_3$ is in position 3 or 4 on the phenyl group.

The substituents are preferentially selected among the halogens, the hydroxyl, cyano, nitroso, nitro, —$CF_3$, alkyl, alkenyl, cycloalkyl, thioalkyl, alkoxy, amino, alkylamino, acyl, aryl, aralkyl groups or a saturated or non-saturated heterocycle.

In a first embodiment, the invention relates to compounds of general formula (II):

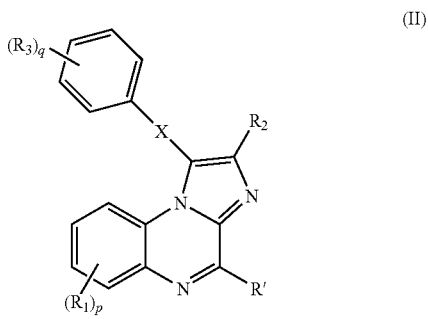

(II)

wherein $R_1$, $R_2$, $R_3$, R', X, p and q are defined above.

In a second embodiment, the invention relates to compounds of general formula (III):

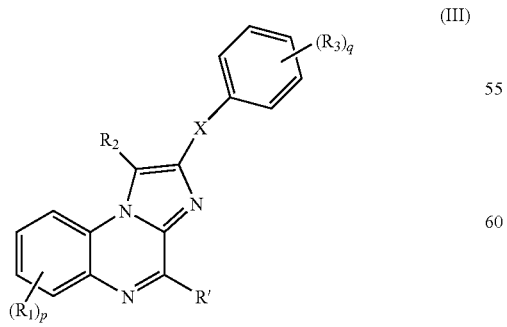

(III)

wherein
$R_1$, $R_2$, $R_3$, R', X, p and q are defined above.

Preferentially, the invention relates to compounds chosen among the following compounds: N-methyl-2-(2-phenylethyl)imidazo[1,2-a]quinoxalin-4-amine, N,N-Dimethyl-2-(2-phenylethyl)imidazo[1,2-a]quinoxalin-4-amine, N-(2-aminoethyl)-2-(2-phenylethyl)imidazo[1,2-a]quinoxalin-4-amine, 2-(2-phenylethyl)imidazo[1,2-a]quinoxalin-4-amine, 4-methoxy-2-(2-phenylethyl)imidazo[1,2-a]quinoxaline, 4-Chloro-2-(2-phenylethyl)imidazo[1,2-a]quinoxaline and their physiologically acceptable salts.

Preferably, the invention relates to compounds of general formula (IV)

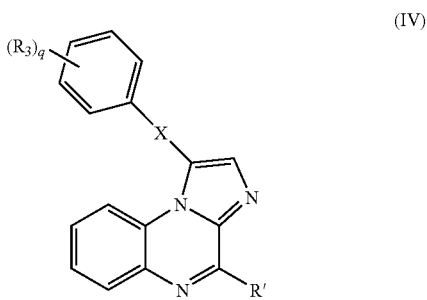

(IV)

wherein $R_3$, R', X and q are defined above.

Preferably, the compounds according to the invention are selected among the following compounds: N-methyl-1-(2-phenylethyl)imidazo[1,2-a]quinoxalin-4-amine, N,N-Dimethyl-1-(2-phenylethyl)imidazo[1,2-a]quinoxalin-4-amine, N-(2-aminoethyl)-1-(2-phenylethyl)imidazo[1,2-a]quinoxalin-4-amine, 1-(2-phenylethyl)imidazo[1,2-a]quinoxalin-4-amine, 4-methoxy-1-(2-phenylethyl)imidazo[1,2-a]quinoxaline, 4-Chloro-1-(2-phenylethyl)imidazo[1,2-a]quinoxaline, 1-(2-phenylethyl)imidazo[1,2-a]quinoxaline-4(5H)-one, 1-(2-phenylethyl)-4-pyrrolidin-1-yl]imidazo[1,2-a]quinoxaline, 1-(2-phenylethyl)-4-piperidin-1-yl]imidazo[1,2-a]quinoxaline, N-phenyl-1-(2-phenylethyl)imidazo[1,2-a]quinoxalin-4-amine, N,1-bis(2-phenylethyl)imidazo[1,2-a]quinoxalin-4-amine, t-butyl-4-[1-(2-phenylethyl)imidazo[1,2-a]quinoxalin-4-yl]piperazine-1-carboxylate, [1-(2-phenylethyl)-4-piperazin-1-yl]imidazo[1,2-a]quinoxaline and their physiologically acceptable salts.

In an advantageous embodiment of the invention, the compounds are of general formula (V):

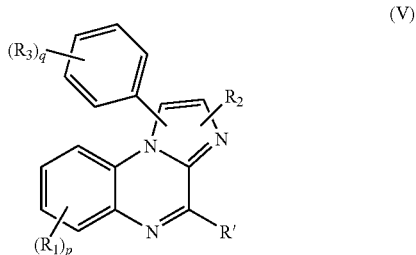

(V)

wherein $R_1$, $R_2$, $R_3$, R', p and q are defined above.

In another embodiment of the invention, the compounds are general formula (VI):

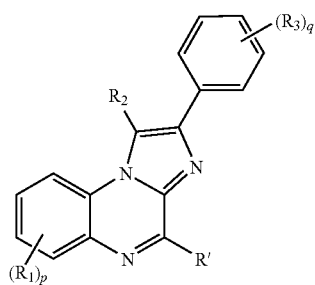

(VI)

wherein R₁, R₂, R₃, R', p and q are defined above.

Preferably, the compounds are of general formula (VII):

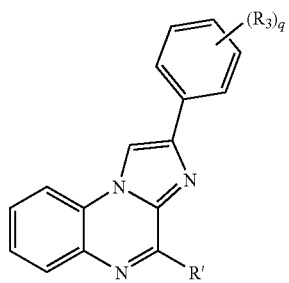

(VII)

wherein R₃, R' and q are defined above.

Preferably, the compounds are selected among the following compounds: N-(2-aminoethyl)-2-(2-hydroxyphenyl)imidazo[1,2-a]quinoxalin-4-amine, N-(2-aminoethyl)-2-(3-hydroxyphenyl)imidazo[1,2-a]quinoxalin-4-amine, N-(2-aminoethyl)-2-(4-hydroxyphenyl)imidazo[1,2-a]quinoxalin-4-amine, N-(2-aminoethyl)-2-(2,4-dihydroxyphenyl)imidazo[1,2-a]quinoxalin-4-amine, N-(2-aminoethyl)-2-(2,3-dihydroxyphenyl)imidazo[1,2-a]quinoxalin-4-amine, N-(2-aminoethyl)-2-(2-methoxyphenyl)imidazo[1,2-a]quinoxalin-4-amine, N-(2-aminoethyl)-2-(3-methoxyphenyl)imidazo[1,2-a]quinoxalin-4-amine, N-(2-aminoethyl)-2-(4-methoxyphenyl)imidazo[1,2-a]quinoxalin-4-amine, N-(2-aminoethyl)-2-(2,4-dimethoxyphenyl)imidazo[1,2-a]quinoxalin-4-amine, N-(2-aminoethyl)-2-(2,3-dimethoxyphenyl)imidazo[1,2-a]quinoxalin-4-amine, N-(2-aminoethyl)-2-(3-ethoxyphenyl)imidazo[1,2-a]quinoxalin-4-amine, N-(2-aminoethyl)-2-(4-ethoxyphenyl)imidazo[1,2-a]quinoxalin-4-amine, N-(2-aminoethyl)-2-(3-bromophenyl)imidazo[1,2-a]quinoxalin-4-amine, N-(2-aminoethyl)-2-(4-bromophenyl)imidazo[1,2-a]quinoxalin-4-amine, N-(2-aminoethyl)-2-(3-(trifluoromethyl)phenyl))imidazo[1,2-a]quinoxalin-4-amine, N-(2-aminoethyl)-2-(4-(trifluoromethyl)phenyl))imidazo[1,2-a]quinoxalin-4-amine, N-(2-aminoethyl)-2-(3-chlorophenyl)imidazo[1,2-a]quinoxalin-4-amine, N-(2-aminoethyl)-2-(4-chlorophenyl)imidazo[1,2-a]quinoxalin-4-amine, N-(2-aminoethyl)-2-(3-carboxyphenyl)imidazo[1,2-a]quinoxalin-4-amine, N-(2-aminoethyl)-2-(4-carboxyphenyl)imidazo[1,2-a]quinoxalin-4-amine, N-(2-aminoethyl)-2-(3-fluorophenyl)imidazo[1,2-a]quinoxalin-4-amine, N-(2-aminoethyl)-2-(4-fluorophenyl)imidazo[1,2-a]quinoxalin-4-amine, N-(2-aminoethyl)-2-(3-cyanophenyl)imidazo[1,2-a]quinoxalin-4-amine, N-(2-aminoethyl)-2-(4-cyanophenyl)imidazo[1,2-a]quinoxalin-4-amine, N-(2-aminoethyl)-2-(3-nitrophenyl)imidazo[1,2-a]quinoxalin-4-amine, N-(2-aminoethyl)-2-(4-nitrophenyl)imidazo[1,2-a]quinoxalin-4-amine, N-(2-aminoethyl)-2-furanimidazo[1,2-a]quinoxalin-4-amine, N-methyl-2-phenylimidazo[1,2-a]quinoxalin-4-amine, N-methyl-2-(2-hydroxyphenyl)imidazo[1,2-a]quinoxalin-4-amine, N-methyl-2-(3-hydroxyphenyl)imidazo[1,2-a]quinoxalin-4-amine, N-methyl-2-(4-hydroxyphenyl)imidazo[1,2-a]quinoxalin-4-amine, N-methyl-2-(2,4-dihydroxyphenyl)imidazo[1,2-a]quinoxalin-4-amine, N-methyl-2-(2,3-dihydroxyphenyl)imidazo[1,2-a]quinoxalin-4-amine, N-methyl-2-(2-methoxyphenyl)imidazo[1,2-a]quinoxalin-4-amine, N-methyl-2-(3-methoxyphenyl)imidazo[1,2-a]quinoxalin-4-amine, N-methyl-2-(4-methoxyphenyl)imidazo[1,2-a]quinoxalin-4-amine, N-methyl-2-(2,4-dimethoxyphenyl)imidazo[1,2-a]quinoxalin-4-amine, N-methyl-2-(2,3-dimethoxyphenyl)imidazo[1,2-a]quinoxalin-4-amine, 2-phenylimidazo[1,2-a]quinoxalin-4-amine, N-methyl-2-(3-ethoxyphenyl)imidazo[1,2-a]quinoxalin-4-amine, N-methyl-2-(4-ethoxyphenyl)imidazo[1,2-a]quinoxalin-4-amine, N-methyl-2-(3-bromophenyl)imidazo[1,2-a]quinoxalin-4-amine, N-methyl-2-(4-bromophenyl)imidazo[1,2-a]quinoxalin-4-amine, N-methyl-2-(3-(trifluoromethyl)phenyl))-imidazo[1,2-a]quinoxalin-4-amine, N-methyl-2-(4-(trifluoromethyl)-phenyl))imidazo[1,2-a]quinoxalin-4-amine, N-methyl-2-(3-chlorophenyl)imidazo[1,2-a]quinoxalin-4-amine, N-methyl-2-(4-chlorophenyl)-imidazo[1,2-a]quinoxalin-4-amine, N-methyl-2-(3-carboxyphenyl)imidazo[1,2-a]quinoxalin-4-amine, N-methyl-2-(4-carboxyphenyl)imidazo[1,2-a]quinoxalin-4-amine, N-methyl-2-(3-fluorophenyl)imidazo[1,2-a]quinoxalin-4-amine, N-methyl-2-(4-fluorophenyl)imidazo[1,2-a]quinoxalin-4-amine, N-methyl-2-(3-cyanophenyl)imidazo[1,2-a]quinoxalin-4-amine, N-methyl-2-(4-cyanophenyl)imidazo[1,2-a]quinoxalin-4-amine, N-methyl-2-(3-nitrophenyl)imidazo[1,2-a]quinoxalin-4-amine, N-methyl-2-(4-nitrophenyl)imidazo[1,2-a]quinoxalin-4-amine, N-methyl-2-furanimidazo[1,2-a]quinoxalin-4-amine, 2-(2-hydroxyphenyl)imidazo[1,2-a]quinoxaline, 2-(3-hydroxyphenyl)imidazo[1,2-a]quinoxaline, 2-(4-hydroxyphenyl)imidazo[1,2-a]quinoxaline, 2-(2,4-dihydroxyphenyl)imidazo[1,2-a]quinoxalin-4-amine, 2-(2,3-dihydroxyphenyl)imidazo[1,2-a]quinoxalin-4-amine, 2-(2-methoxyphenyl)imidazo[1,2-a]quinoxalin-4-amine, 2-(3-methoxyphenyl)imidazo[1,2-a]quinoxalin-4-amine, 2-(4-methoxyphenyl)imidazo[1,2-a]quinoxalin-4-amine, 2-(2,4-dimethoxyphenyl)imidazo[1,2-a]quinoxalin-4-amine, 2-(2,3-dimethoxyphenyl)imidazo[1,2-a]quinoxalin-4-amine, 2-(3-ethoxyphenyl)imidazo[1,2-a]quinoxalin-4-amine, 2-(4-ethoxyphenyl)imidazo[1,2-a]quinoxalin-4-amine, 2-(3-bromophenyl)imidazo[1,2-a]quinoxalin-4-amine, 2-(4-bromophenyl)imidazo[1,2-a]quinoxalin-4-amine, 2-(3-(trifluoromethyl)phenyl))imidazo[1,2-a]quinoxalin-4-amine, 2-(4-(trifluoromethyl)phenyl))imidazo[1,2-a]quinoxalin-4-amine, 2-(3-chlorophenyl)imidazo[1,2-a]quinoxalin-4-amine, 2-(4-chlorophenyl)imidazo[1,2-a]quinoxalin-4-amine, 2-(3-carboxyphenyl)imidazo[1,2-a]quinoxalin-4-amine, 2-(4-carboxyphenyl)imidazo[1,2-a]quinoxalin-4-amine, 2-(3-fluorophenyl)imidazo[1,2-a]quinoxalin-4-amine, 2-(4-fluorophenyl)imidazo[1,2-a]quinoxalin-4-amine, 2-(3-cyanophenyl)imidazo[1,2-a]quinoxalin-4-amine, 2-(4-cyanophenyl)imidazo[1,2-a]quinoxalin-4-amine, 2-(3-nitrophenyl)imidazo[1,2-a]quinoxalin-4-amine, 2-(4-nitrophenyl)imidazo[1,2-a]quinoxalin-4-amine, 2-furanimidazo[1,2-a]quinoxalin-4-amine, 4-Chloro-2-phenylimidazo[1,2-a]quinoxaline, 4-Chloro-2-(2-hydroxyphenyl)imidazo[1,2-a]quinoxaline, 4-Chloro-2-(3-hydroxyphenyl)imidazo[1,2-a]quinoxaline, 4-Chloro-2-(4-hydroxyphenyl)imidazo[1,2-a]quinoxaline, 4-Chloro-2-(2-methoxyphenyl)imidazo[1,2-a]quinoxaline, 4-Chloro-2-(3-methoxyphenyl)imidazo[1,2-a]quinoxaline, 4-Chloro-2-(4-methoxyphenyl)imidazo[1,2-a]quinoxaline, 4-Chloro-2-(2,4-dimethoxyphenyl)-imidazo[1,2-a]quinoxaline, 4-Chloro-2-(2,3-dimethoxyphenyl)imidazo[1,2-a]quinoxaline, 4-methoxy-2-phenylimidazo[1,2-a]quinoxaline, 4-methoxy-2-(2-hydroxyphenyl)-imidazo[1,2-a]quinoxaline, 4-methoxy-2-(3-hydroxyphenyl)imidazo[1,2-a]quinoxaline, 4-methoxy-2-(4-hydroxyphenyl)imidazo[1,2-a]quinoxaline, 4-methoxy-2-(2-methoxyphenyl)imidazo[1,2-a]quinoxaline, 4-methoxy-2-(3-methoxyphenyl)imidazo[1,2-a]quinoxaline, 4-methoxy-2-(4-methoxyphenyl)imidazo[1,2-a]quinoxaline, 4-methoxy-2-(2,4-dimethoxyphenyl)imidazo[1,2-a]quinoxaline, 4-methoxy-2-(2,3-dimethoxyphenyl)imidazo[1,2-a]quinoxaline, and their physiologically acceptable salts.

In one embodiment of the invention, the compounds are of general formula (VIII):

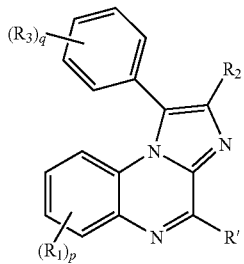

wherein $R_1$, $R_2$, $R_3$, R', p and q are defined above.

Preferably, the compounds are of general formula (IX):

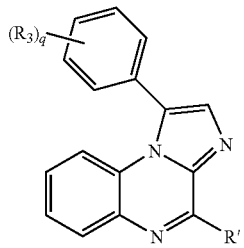

wherein $R_3$, R' and q are defined above.

Preferably, the compounds are selected among the following compounds: N-methyl-1-phenylimidazo[1,2-a]quinoxalin-4-amine, N-methyl-1-(2-hydroxyphenyl)imidazo[1,2-a]quinoxalin-4-amine, N-methyl-1-(3-hydroxyphenyl)imidazo[1,2-a]quinoxalin-4-amine, N-methyl-1-(4-hydroxyphenyl)imidazo[1,2-a]quinoxalin-4-amine, N-methyl-1-(2,4-dihydroxyphenyl)imidazo[1,2-a]quinoxalin-4-amine, N-methyl-1-(2,3-dihydroxyphenyl)imidazo[1,2-a]quinoxalin-4-amine, N-methyl-1-(2-methoxyphenyl)imidazo[1,2-a]quinoxalin-4-amine, N-methyl-1-(3-methoxyphenyl)imidazo[1,2-a]quinoxalin-4-amine, N-methyl-1-(4-methoxyphenyl)imidazo[1,2-a]quinoxalin-4-amine, N-methyl-1-(2,4-dimethoxyphenyl)imidazo[1,2-a]quinoxalin-4-amine, N-methyl-1-(2,3-dimethoxyphenyl)imidazo[1,2-a]quinoxalin-4-amine, N-methyl-1-(3-ethoxyphenyl)imidazo[1,2-a]quinoxalin-4-amine, N-methyl-1-(4-ethoxyphenyl)imidazo[1,2-a]quinoxalin-4-amine, N-methyl-1-(3-bromophenyl)imidazo[1,2-a]quinoxalin-4-amine, N-methyl-1-(4-bromophenyl)imidazo[1,2-a]quinoxalin-4-amine, N-methyl1-(3-(trifluoromethyl)phenyl))imidazo[1,2-a]quinoxalin-4-amine, N-methyl-1-(4-(trifluoromethyl)phenyl))imidazo[1,2-a]quinoxalin-4-amine, N-methyl-1-(3-chlorophenyl)imidazo[1,2-a]quinoxalin-4-amine, N-methyl-1-(4-chlorophenyl)imidazo[1,2-a]quinoxalin-4-amine, N-methyl-1-(3-carboxyphenyl)imidazo[1,2-a]quinoxalin-4-amine, N-methyl-1-(4-carboxyphenyl)imidazo[1,2-a]quinoxalin-4-amine, N-methyl-1-(3-fluorophenyl)imidazo[1,2-a]quinoxalin-4-amine, N-methyl-1-(4-fluorophenyl)imidazo[1,2-a]quinoxalin-4-amine, N-methyl-1-(3-cyanophenyl)imidazo[1,2-a]quinoxalin-4-amine, N-methyl-1-(4-cyanophenyl)imidazo[1,2-a]quinoxalin-4-amine, N-methyl-1-(3-nitrophenyl)imidazo[1,2-a]quinoxalin-4-amine, N-methyl-1-(4-nitrophenyl)imidazo[1,2-a]quinoxalin-4-amine, N-methyl-1-furanimidazo[1,2-a]quinoxalin-4-amine, N-(2-aminoethyl)-1-(2-hydroxyphenyl)imidazo[1,2-a]quinoxalin-4-amine, N-(2-aminoethyl)-1-(3-hydroxyphenyl)imidazo[1,2-a]quinoxalin-4-amine, N-(2-aminoethyl)-1-(4-hydroxyphenyl)imidazo[1,2-a]quinoxalin-4-amine, N-(2-aminoethyl)-1-(2,4-dihydroxyphenyl)imidazo[1,2-a]quinoxalin-4-amine, N-(2-aminoethyl)-1-(2,3-dihydroxyphenyl)imidazo[1,2-a]quinoxalin-4-amine, N-(2-aminoethyl)-1-(2-methoxyphenyl)imidazo[1,2-a]quinoxalin-4-amine, N-(2-aminoethyl)-1-(3-methoxyphenyl)imidazo[1,2-a]quinoxalin-4-amine, N-(2-aminoethyl)-1-(4-methoxyphenyl)imidazo[1,2-a]quinoxalin-4-amine, N-(2-aminoethyl)-1-(2,4-dimethoxyphenyl)imidazo[1,2-a]quinoxalin-4-amine, N-(2-aminoethyl)-1-(2,3-dimethoxyphenyl)imidazo[1,2-a]quinoxalin-4-amine, N-(2-aminoethyl)-1-(3-ethoxyphenyl)imidazo[1,2-a]quinoxalin-4-amine, N-(2-aminoethyl)-1-(4-ethoxyphenyl)imidazo[1,2-a]quinoxalin-4-amine, N-(2-aminoethyl)-1-(3-bromophenyl)imidazo[1,2-a]quinoxalin-4-amine, N-(2-aminoethyl)-1-(4-bromophenyl)imidazo[1,2-a]quinoxalin-4-amine, N-(2-aminoethyl)-1-(3-(trifluoromethyl)phenyl))imidazo[1,2-a]quinoxalin-4-amine, N-(2-aminoethyl)-1-(4-(trifluoromethyl)phenyl))imidazo[1,2-a]quinoxalin-4-amine, N-(2-aminoethyl)-1-(3-chlorophenyl)imidazo[1,2-a]quinoxalin-4-amine, N-(2-aminoethyl)-1-(4-chlorophenyl)imidazo[1,2-a]quinoxalin-4-amine, N-(2-aminoethyl)-1-(3-carboxyphenyl)imidazo[1,2-a]quinoxalin-4-amine, N-(2-aminoethyl)-1-(4-carboxyphenyl)imidazo[1,2-a]quinoxalin-4-amine, N-(2-aminoethyl)-1-(3-fluorophenyl)imidazo[1,2-a]quinoxalin-4-amine, N-(2-aminoethyl)-1-(4-fluorophenyl)imidazo[1,2-a]quinoxalin-4-amine, N-(2-aminoethyl)-1-(3-cyanophenyl)imidazo[1,2-a]quinoxalin-4-amine, N-(2-aminoethyl)-1-(4-cyanophenyl)imidazo[1,2-a]quinoxalin-4-amine, N-(2-aminoethyl)-1-(3-nitrophenyl)imidazo[1,2-a]quinoxalin-4-amine, N-(2-aminoethyl)-1-(4-nitrophenyl)imidazo[1,2-a]quinoxalin-4-amine, N-(2-aminoethyl)-1-furanimidazo[1,2-a]quinoxalin-4-amine, 1-phenylimidazo[1,2-a]quinoxalin-4-amine, 1-(2-hydroxyphenyl)imidazo[1,2-a]quinoxaline, 1-(3-hydroxyphenyl)imidazo[1,2-a]quinoxaline, 1-(4-hydroxyphenyl)imidazo[1,2-a]quinoxaline, 1-(2,4-dihydroxyphenyl)imidazo[1,2-a]quinoxalin-4-amine, 1-(2,3-dihydroxyphenyl)imidazo[1,2-a]quinoxalin-4-amine, 1-(2-methoxyphenyl)imidazo[1,2-a]quinoxalin-4-amine, 1-(3-methoxyphenyl)imidazo[1,2-a]quinoxalin-4-amine, 1-(4-methoxyphenyl)imidazo[1,2-a]quinoxalin-4-amine, 1-(2,4-dimethoxyphenyl)imidazo[1,2-a]quinoxalin-4-amine, 1-(2,3-dimethoxyphenyl)imidazo[1,2-a]quinoxalin-4-amine, 1-(3-ethoxyphenyl)imidazo[1,2-a]quinoxalin-4-amine, 1-(4-ethoxyphenyl)imidazo[1,2-a]

quinoxalin-4-amine, 1-(3-bromophenyl)imidazo[1,2-a]quinoxalin-4-amine, 1-(4-bromophenyl)imidazo[1,2-a]quinoxalin-4-amine, 1-(3-(trifluoromethyl)phenyl))imidazo[1,2-a]quinoxalin-4-amine, 1-(4-(trifluoromethyl)phenyl))imidazo[1,2-a]quinoxalin-4-amine, 1-(3-chlorophenyl) imidazo[1,2-a]quinoxalin-4-amine, 1-(4-chlorophenyl) imidazo[1,2-a]quinoxalin-4-amine, 1-(3-carboxyphenyl) imidazo[1,2-a]quinoxalin-4-amine, 1-(4-carboxyphenyl) imidazo[1,2-a]quinoxalin-4-amine, 1-(3-fluorophenyl) imidazo[1,2-a]quinoxalin-4-amine, 1-(4-fluorophenyl) imidazo[1,2-a]quinoxalin-4-amine, 1-(3-cyanophenyl) imidazo[1,2-a]quinoxalin-4-amine, 1-(4-cyanophenyl) imidazo[1,2-a]quinoxalin-4-amine, 1-(3-nitrophenyl) imidazo[1,2-a]quinoxalin-4-amine, 1-(4-nitrophenyl) imidazo[1,2-a]quinoxalin-4-amine, 1-furanimidazo[1,2-a] quinoxalin-4-amine, 4-Chloro-1-phenylimidazo[1,2-a] quinoxaline, 4-Chloro-1-(2-hydroxyphenyl)imidazo[1,2-a] quinoxaline, 4-Chloro-1-(3-hydroxyphenyl)imidazo[1,2-a] quinoxaline, 4-Chloro-1-(4-hydroxyphenyl)imidazo[1,2-a] quinoxaline, 4-Chloro-1-(2-methoxyphenyl)imidazo[1,2-a] quinoxaline, 4-Chloro-1-(3-methoxyphenyl)imidazo[1,2-a] quinoxaline, 4-Chloro-1-(4-methoxyphenyl)imidazo[1,2-a] quinoxaline, 4-Chloro-1-(2,4-dimethoxyphenyl)imidazo[1,2-a]quinoxaline, 4-Chloro-1-(2,3-dimethoxyphenyl)imidazo[1,2-a]quinoxaline, 4-methoxy-1-phenylimidazo[1,2-a] quinoxaline, 4-methoxy-1-(2-hydroxyphenyl)imidazo[1,2-a]quinoxaline, 4-methoxy-1-(3-hydroxyphenyl)imidazo[1,2-a]quinoxaline, 4-methoxy-1-(4-hydroxyphenyl)imidazo[1,2-a]quinoxaline, 4-methoxy-1-(2-methoxyphenyl)imidazo[1,2-a]quinoxaline, 4-methoxy-1-(3-methoxyphenyl)imidazo[1,2-a]quinoxaline, 4-methoxy-1-(4-methoxyphenyl)imidazo[1,2-a]quinoxaline, 4-methoxy-1-(2,4-dimethoxyphenyl)imidazo[1,2-a]quinoxaline, 4-methoxy-1-(2,3-dimethoxyphenyl)imidazo[1,2-a]quinoxaline, and their physiologically acceptable salts.

Another object of the present invention is the use of a compound of general formula (X):

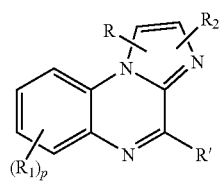

(X)

wherein
R, R', $R_1$, and $R_2$ represent independently an atom of hydrogen, a halogen or a group chosen among the hydroxy, alkyl, alkenyl, cycloalkyl, thioalkyl, alkoxy, amino, alkylamino, dialkylamino, acyl, aryl, aralkyl radicals or a saturated or non-saturated heterocycle, optionally substituted by one or more substituents, and the cyano, nitroso, nitro, —$CF_3$, —$(CH_2)_nNR_4R_5$, —$(CH_2)_nCO$—$NR_4R_5$, —$(CH_2)_nSO_2$—$NR_4R_5$, ou —$(CH_2)_nCO_2R_4$, —NH—$(CH_2)_nNR_4R_5$ radicals,
N being independently between 0 and 4,
p ranging between 1 and 4,
$R_4$ and $R_5$ representing independently an atom of hydrogen or group chosen among the linear or branched $C_1$-$C_4$ alkyl, linear or branched alkenyl, $C_3$-$C_7$ cycloalkyl, acyl, aryl, aralkyl radicals or a heterocycle, optionally substituted by one or more physiologically acceptable substituents, and salts thereof, for the preparation of a drug intended for the treatment of lymphomas.

Preferably, R, $R_1$ and $R_2$ represent a hydrogen atom, a halogen or a group chosen among the methyl, ethyl, propyl, isopropyl, butyl, isobutyl, tertiobutyl, and —$(CH_2)_{n''}$—(CH═CH)—$(CH_2)_{n'''}$—$CH_3$ with N" and n''' independently between 0 and 4, $COOR_4$, $NR_4R_5$ and $OR_5$, $R_4$ and $R_5$ are defined above.
R' represents independently an atom of hydrogen, a halogen or a group chosen among the hydroxy, alkoxy, alkylamino, dialkylamino groups, a saturated or non-saturated heterocycle and —NH—$(CH_2)_nNR_4R_5$.
Preferentially, $R_2$ is a hydrogen atom.
Preferably, R' is a chloro, methoxy, amino, methylamino, dimethylamino, ethylamino, diethylamino, aminomethylamine or aminoethylamine group. Preferentially, R' is —NH—$CH_3$, —$NH_2$ or —NH—$(CH_2)_2$—$NH_2$.
Preferentially, R is selected among the methyl, ethyl, propyl, isopropyl, butyl, isobutyl, tertiobutyl and —$(CH_2)_{n''}$—(CH═CH)—$(CH_2)_{n'''}$—$CH_3$ groups with n" and n''' independently between 0 and 4.
In a particular embodiment of the invention, the compound used is of general formula (XI):

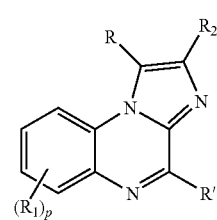

(XI)

wherein R, R', $R_1$, and $R_2$ and p are defined above.
Preferably, the invention relates to the use of a compound chosen among the following compounds: 1-isobutylimidazo[1,2-a]quinoxalin-4-amine, N-methyl-1-isobutyl imidazo[1,2-a]quinoxalin-4-amine, N,N-dimethyl-1-isobutylimidazo[1,2-a]quinoxalin-4-amine, N-(2-aminoethyl)-1-isobutylimidazo[1,2-a]quinoxalin-4-amine, 4-Chloro-1-isobutylimidazo[1,2-a]quinoxaline and 1-isobutyl-4-methoxyimidazo[1,2-a]quinoxaline and their physiologically acceptable salts.
In another embodiment, the use relates to a compound of general formula (XII):

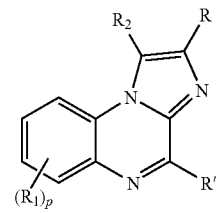

(XII)

wherein R, R', $R_1$, $R_2$ and p are defined above.
Preferentially, the invention relates to the use of a compound chosen among the following compounds: N-methyl-2-isobutylimidazo[1,2-a]quinoxalin-4-amine, N,N-dimethyl-2-isobutylimidazo[1,2-a]quinoxalin-4-amine, N-(2-aminoethyl)-2-isobutylimidazo[1,2-a]quinoxalin-4-amine 4-Chloro-2-isobutylimidazo[1,2-a]quinoxaline and 2-isobutyl-4-methoxyimidazo[1,2-a]quinoxaline and their physiologically acceptable salts.

Preferentially, the invention relates to the inventive compounds for use as drug.

More preferentially, the invention relates to the inventive compounds for use as drug for the treatment of cancers.

Still more preferentially, the invention relates to the inventive compounds for the treatment of melanomas or lymphomas.

The invention also relates to a pharmaceutical composition that includes a compound such as defined above and a suitable pharmaceutical carrier.

Another object of the present invention is a product that includes a compound such as defined above and another active agent as a combination product for simultaneous, separated or extended use over time in therapy.

The invention also relates to the use of a compound such as defined above for the preparation of a drug intended for the treatment of cancers. More preferentially, to the use of a compound according to the invention for the preparation of a drug intended for the treatment of melanomas or lymphomas.

In an advantageous embodiment, the inventive compounds are used in combination with at least one other active agent.

The invention also relates to methods of therapeutic treatment of cancers including the administration of an effective quantity of a compound (or a physiologically acceptable salt of a compound) according to the invention in an individual. Preferably, the invention relates to methods of therapeutic treatment of melanomas and lymphomas.

Halogen means in particular according to the present invention the following halogens: F, Cl, Br and I.

Alkyl means in particular according to the present invention the linear or branched alkyl radicals, in particular the C1, C2, C3, C4, C5 or C6 alkyl radicals, in particular the methyl, ethyl, n-propyl, i-propyl, n-butyl, i-butyl or t-butyl radicals. This definition also applies to the alkyl portions of cycloalkyl, alkoxy, acyl, aralkyl, alkylamino, thioalkyl radicals.

Alkenyl preferably means according to the invention a hydrocarbon, monovalent, unsaturated and including at least one double bond, linear or branched chain, comprising from 2 to 6 carbon atoms, whose representative elements are for example the vinyl groups, 1-propenyl, 2-propenyl, isoprenyl, butenyl, pentenyl, hexenyl.

Cycloalkyl advantageously means according to the invention $C_1$-$C_7$ cycloalkyls, more particularly cyclopropyl, cyclobutyl, cyclopentyl, cyclohexyl and cycloheptyl radicals.

Aryl preferably means according to the invention one or more aromatic rings having 6 to 10 carbon atoms, being able to be joined or combined, in particular phenyl. This definition also applies to the aryl part of aralkyl radicals. The aralkyl group is preferably $(CH_2)_n$-phenyl wherein n is between 0 and 4.

Amino or amine means a primary, secondary or tertiary amine.

Heterocycle advantageously means according to the invention a $C_3$-$C_7$ ring containing at least one heteroatom chosen among nitrogen, oxygen or sulphur, in particular the heterocycles are selected among thienyl, furyl, quinolinyl, indolyl, pyrazole, pyrrole, pyridine, pyrimidine, imidazol.

"Cancer" means all malignant neoplastic formations, whatever the histological nature. There are two main categories of malignant tumours: carcinomas, of epithelial origin, and the sarcomas, of conjunctive origin. Malignant tumours are made up of atypical cells, invading or disseminating, generally characterised by the ability to grow autonomously, imprecise delimitation, an ability to invade nearby tissues and vessels and a tendency to disseminate by the production of metastases. Notable cancers include cancers of the breast, prostate, lungs, oesophagus, skin, bladder, stomach, liver, uterus, colon and rectum.

"Melanoma" means a malignant tumour that develops at the expense of pigmented tissues, those of the skin or the eye more especially.

"Lymphoma" means any tumour, generally malignant, due to a proliferation of cells of lymphoid tissue, developing especially on the level of the spleen or the ganglia.

Pharmaceutically acceptable salt preferably means according to the invention a salt of a pharmaceutically acceptable acid, i.e., with any non-toxic acid, including organic and inorganic acids. Such acids include acetic, benzenesulphonic, benzoic, citric, ethanesulphonic, fumaric, gluconic, glutamic, hydrobromic, hydrochloric, lactic, maleic, malic, mandelic, methanesulphonic, mucic, nitric, pamoic, pantothenic, phosphoric, succinic, sulphuric, tartaric and paratoluenesulphonic acid.

The invention relates to a pharmaceutical composition that includes a compound such as defined above and a suitable pharmaceutical carrier.

These compositions can be formulated for administration in mammals, including man. Dosing varies according to the treatment and the affection in question. These compositions are produced in such a way as to be able to be administered by digestive or parenteral route.

In the pharmaceutical compositions of the present invention for oral, sublingual, subcutaneous, intramuscular, intravenous, transdermal, local or rectal administration, the active ingredient can be administered in unit dose forms of administration, in mixture with traditional pharmaceutical carriers, in animals or human beings. Suitable unit dose forms of administration include forms by oral route such as tablets, gelatine capsules, powders, granules and oral solutions or suspensions, forms for sublingual and oral administration, subcutaneous, intramuscular, intravenous, intranasal or intraocular forms of administration and rectal forms of administration.

When a solid composition is prepared in tablet form, the principal active ingredient is mixed with a pharmaceutical carrier such as gelatine, starch, lactose, magnesium stearate, talc, gum arabic or analogues. The tablets can be coated with saccharose or other suitable materials or they can be treated so that they have prolonged or delayed activity and that they release continuously a predetermined quantity of active ingredient.

A preparation in gelatine capsules is obtained by mixing the active ingredient with a diluent and by pouring the mixture obtained into soft or hard gelatine capsules.

A preparation in syrup or elixir form can contain the active ingredient in conjunction with a sweetening substance, an antiseptic, as well as an agent giving taste and a suitable colour.

Powders or granules dispersible in water can contain the active ingredient mixed with dispersion agents or wetting agents, or suspension agents, just as with taste correctors or sweetening substances.

The inventive compounds can be employed in therapy only, or in combination with at least one other active agent. These other active agents are in particular selected among the suitable active ingredients for the treatment of cancers. They can be adjuvants to improve the activity of the inventive compound, or of other active ingredients known for their use in the treatment of such affections. Such active agents are well known to the person skilled in the art and are available commercially or are described in reference works such as Le Dictionnaire Vidal, published with updates each year, in particular the active agents grouped in the "Cancerologie Hematologie" pharmacotherapeutic families.

The present invention thus also relates to a product that includes a compound according to the invention and another active agent as a combination product for simultaneous, separated or extended use over time in therapy, and in particular in the treatment of cancers.

The inventive compounds can be prepared according to various modes of preparation described below and in the examples.

Synthesis 1: Imidazo[1,2-a]quinoxaline derivatives were obtained by condensation between an α-aminoalcohol and quinoxaline, followed by intramolecular cyclization and various nucleophilic substitutions. α-Cyanoalcools (2-hydroxy-4-methylpentanenitrile or 2-hydroxy-4-phenylbutanenitrile) result from the reaction between isovaleraldehyde in series a or 3-phenylpropionaldehyde in series b, and sodium cyanide. They are then reduced using lithium aluminium hydride to yield the corresponding α-aminoalcohols (either 1-amino-4-methylpentan-2-ol 1a, or 1-amino-4-phenylbutan-2-ol 1b). 1a and 1b are then condensed with 2,3-dichloroquinoxaline in the presence of triethylamine in dioxane to form 1-[(3-chloroquinoxalin-2-yl)amino]-4-methylpentan-2-ol 2a and 1-[(3-chloroquinoxalin-2-yl)amino]-4-phenylbutan-2-ol 2b. Oxidation of these two compounds by the complex sulphur trimethylamine trioxide is necessary to allow their intramolecular cyclization and to obtain the derivatives 4a and 4b, respectively. Lastly, nucleophilic substitution is carried out on the two chlorinated derivatives to yield 5b, 6a, 6b, 7a, 7b, 8b according to the nature of the R group (see diagram below).

Synthesis 2: Dimer 9 diimidazo[1,2-a]:[1',5'-d]piperazine-5,10-dione results from the bimolecular condensation of imidazo-2-carboxylic acid in the presence of thionyl chloride. It is then coupled with orthofluoroaniline to give intermediate 10. Construction of tricyclic compound 11 is achieved by intramolecular cyclization of 10, in the presence of sodium hydride in dimethylacetamide. A chlorination step followed by substitution with methylamine leads to compound 13. Compound 13 is then brominated by N-bromosuccinimide to give brominated compound 14, which in turn will be substituted by alkyl groups via Suzuki reactions to yield compounds 15a to 15n (see diagram below).

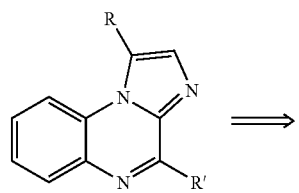

5b (EAPB0202)   5: R' = NH$_2$
6a (EAPB0103)
6b (EAPB0203)   6: R' = NHCH$_3$
7a (EAPB0104)   7: R' = N(CH$_3$)$_2$
7b (EAPB0204)
8b (EAPB0206)   8: R' = OCH$_3$

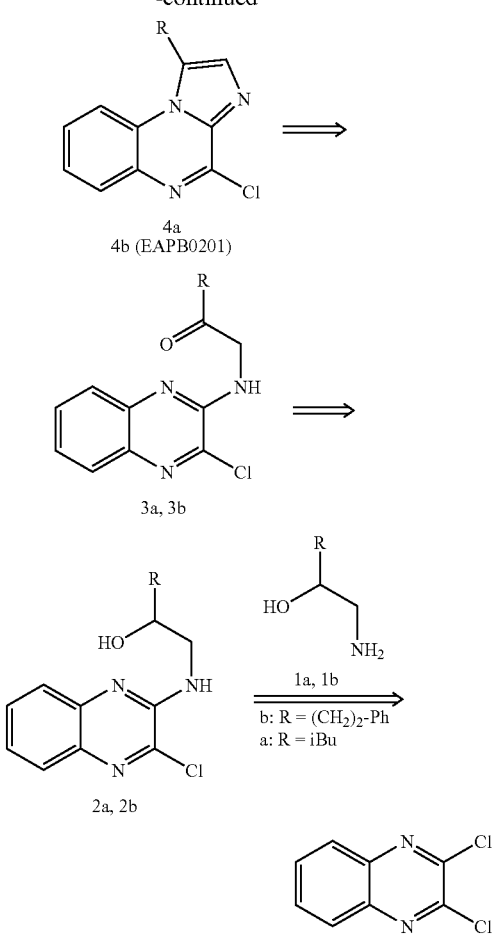

Synthesis 1 of the imidazo[1,2-a]quinoxaline Series

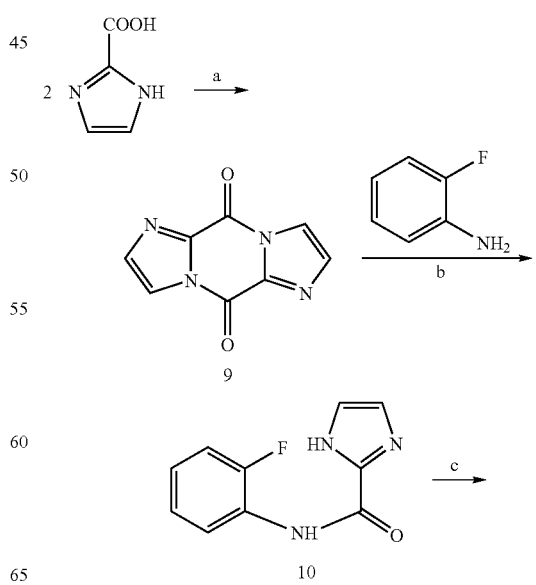

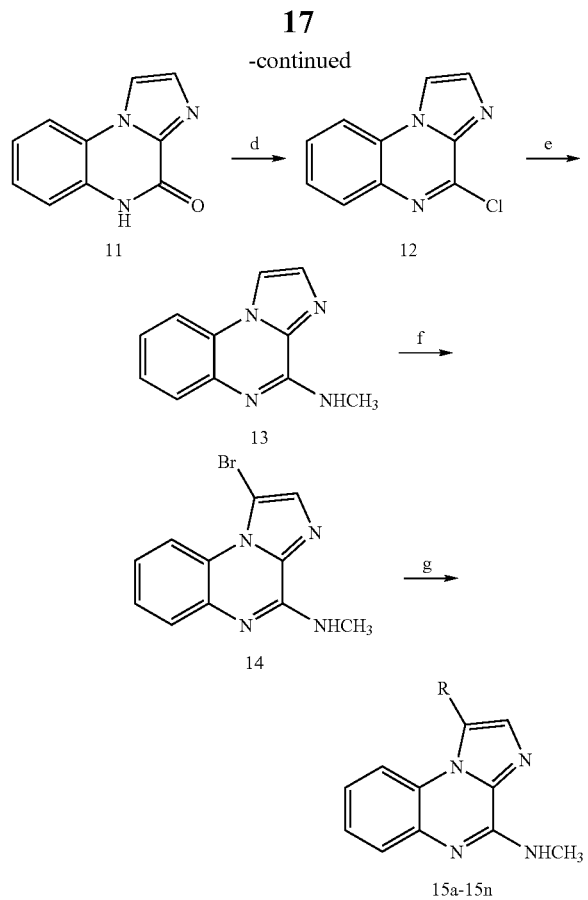

Synthesis 2 of the 1H-imidazo[1,2-a]quinoxaline Series

Reagents and conditions: (a) SOCl$_2$ reflux, 18 h; (b) NaH-MDS, THF, 5 h; (c) NaH, DMA, reflux, 10 h; (d) POCl$_3$, reflux, 6 h; (e) EtOH, NHCH$_3$, 20 h, rt; (f) NBS, CHCl$_3$, reflux, 2 h; (g) arylboronic acid (R$_1$—B(OH)$_2$), Pd(PPh$_3$)$_4$, Na$_2$CO$_3$, DME, MW (140° C., 20 min).

FIGURES

FIG. 1: Effects of fotemustine (20 mg/kg once per week for 3 weeks) and EAPB0203 (20 mg/kg twice per week for 3 weeks) on tumour growth in athymic Swiss mice xenografted with M4Be human melanoma cell line.
▼, administrations of fotemustine and EAPB10203; administrations of EAPB0203.
Δ, control; ■, EAPB0203; ●, fotemustine. The data are the results of only one experiment carried out on six mice per group. The results are represented as mean±SEM.
Significant difference between the three treatment groups: *, p<0.05; , 0.002<p<0.009; *, p≦0.001.

Figure 2:
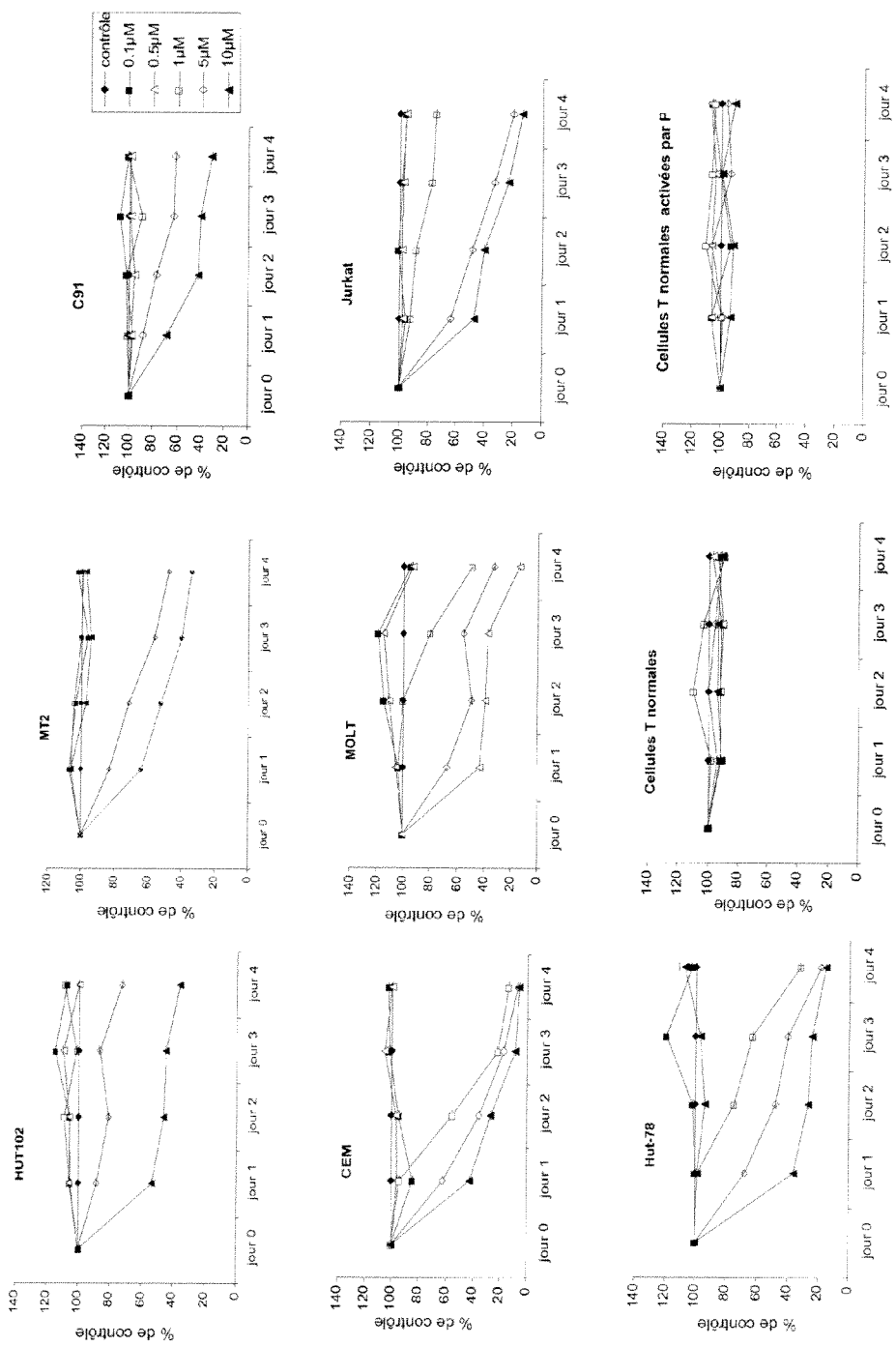

FIG. 2: HTLV-I-positive and HTLV-I-negative malignant human cell lines are sensitive to EAPB0203, but activated or inactivated normal T lymphocytes are resistant. Effects of EAPB0203 on the growth of human T lines not infected by HTLV-I (CEM, Jurkatt, Molt-4 and HuT-78), HTLV-I-positive human T lines (HuT-102 and C8166, and MT2), and normal lymphocytes at rest or activated by PHA. The activated normal PBMC were supplemented with 2% PHA. EAPB0203 was added at the concentrations indicated in mole/l for 24-96 h. Cell growth is analyzed with the "CellTi-ter 96®" nonradioactive cell growth kit. The results are expressed as a percentage of the control (0.1% DMSO) and represent the mean of the results obtained in three independent experiments.

Figure 3:
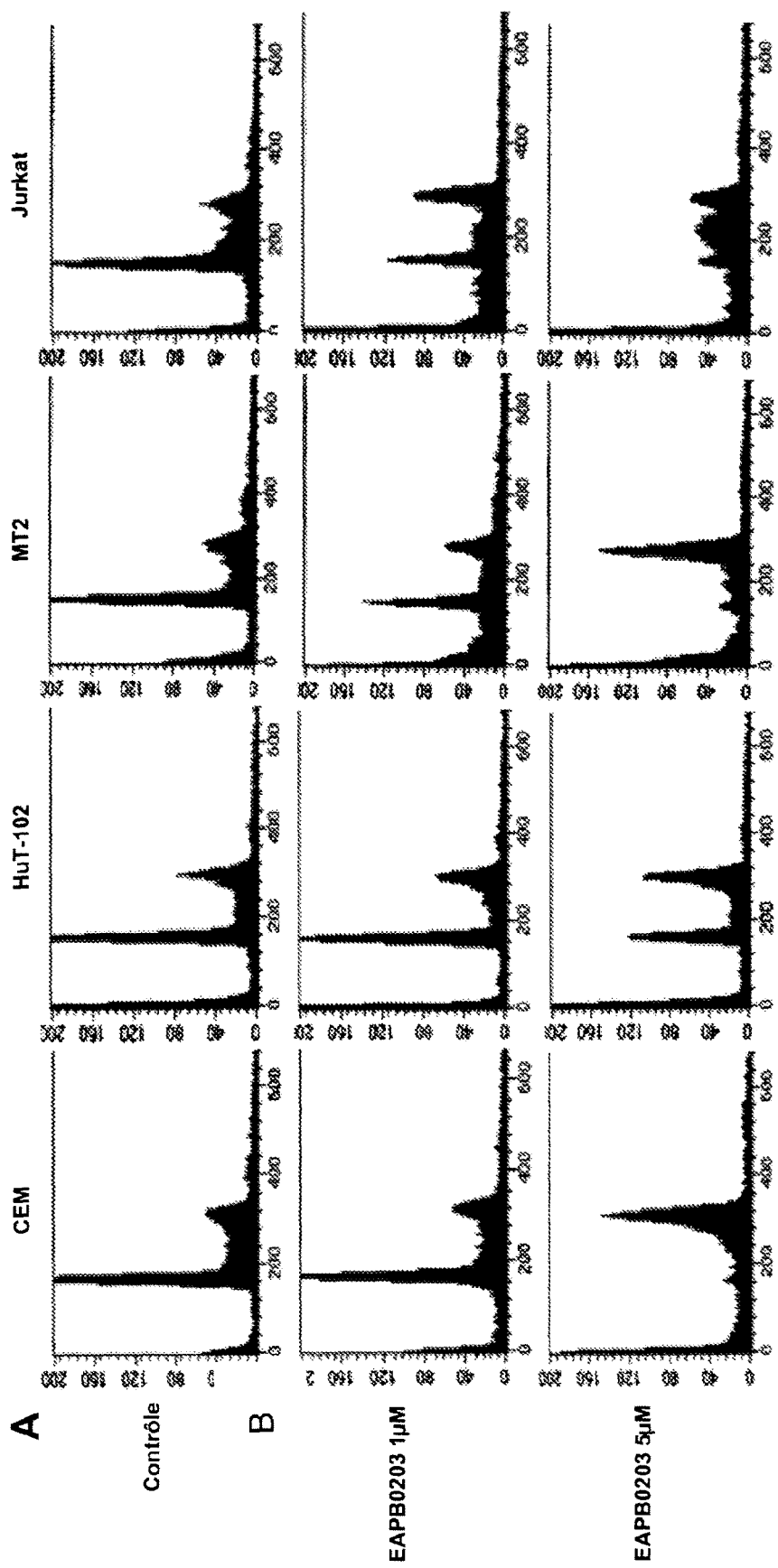

FIG. 3: EAPB0203 induces the termination of the cell cycle in phase G2/M in human HTLV-I-positive and HTLV-I-negative T-cell lines. (A) Effects of EAPB0203 on the distribution of the cell cycle of CEM, HuT-102, MT2, and Jurkatt cells. The cells treated by EAPB0203 were marked with propidium iodide (50 mg/ml) and analysis of the cellular cycle was carried out by FACScan flow cytometry. (b) The pre-G1 percentage represents the apoptotic cells. (c) The cells in cycle, the sum of phases (S+G2/M), are represented as a percentage of non-apoptotic cells. The results represent two independent experiments.

EXAMPLES

1) Synthesis of imidazo[1,2-a]quinoxaline Compounds

2-Hydroxy-4-methylpentanenitrile 10 g (116 mmol) of isovaleraldehyde are added over 2 or 3 minutes to a solution of 37% aqueous NaHSO$_3$ (25 ml, 116 mmol), at 0° C., and under stirring. A white bisulphite precipitate is formed almost immediately. A solution of NaCN (5.7 g, 116 mmol) in H$_2$O (30 ml) is then added dropwise, over 45 min. Stirring is maintained for 18 h at room temperature; during this time the precipitate was solubilized and two non-miscible layers were formed. The mixture is extracted in Et$_2$O (30 ml). The ether phases are collected, dried by Na$_2$SO$_4$ and evaporated to give a yellow oil used with no other purification (12.21 g, 93%); $^1$H NMR (100 MHz, CDCl$_3$) δ: 0.88 (d, J=6 Hz, 6H), 1.51-1.98 (m, 3H, H-3+H-4), 4.20 (s, Br, OH), 4.45 (t, J=7 Hz, 1H); $^{13}$C NMR (25 MHz, DMSO-d$_6$) δ: 21.6, 22.1, 23.8, 43.1, 58.3, 121.3. Analysis calculated for C$_6$H$_{11}$NO: C, 63.68; H, 9.80; N, 12.38. Experimental: C, 63.56; H, 9.75; N, 12.42.

2-Hydroxy-4-phenylbutanenitrile

2-Hydroxy-4-phenylbutanenitrile is prepared from 3-phenylpropionaldehyde according to the protocol described for 2-Hydroxy-4-methylpentanenitrile; (11.14 g, 83.2 mmol) 3-phenylpropionaldehyde, NaHSO$_3$ (17.7 ml of solution at 37%, 83 mmol), (4.08 g, 83.2 mmol) of NaCN in H$_2$O (18 ml). The product, a yellow oil, is used with no other purification (12.4 g, 93%); $^1$H NMR (100 MHz, CDCl$_3$) δ: 2.02-2.25 (m, 2H), 2.76-2.91 (m, 2H), 3.98 (s, 1H), 4.39 (t, J=8 Hz, 1H), 7.26 (d, J=3 Hz, 5H); $^{13}$C NMR (25 MHz, CDCl$_3$) δ: 30.49, 36.37, 59.92, 120.04, 126.28, 128.28, 128.49, 139.60. Analysis calculated for C$_{10}$H$_{11}$NO: C, 74.51; H, 6.88; N, 8.69. Experimental: C, 74.38; H, 6.97; N, 8.42.

1-Amino-4-methylpentan-2-ol (1a)

A solution of 2-hydroxy-4-methylpentanenitrile (12.13 g, 107 mmol) dissolved in Et$_2$O (50 ml) is added dropwise over 45 minutes, with light reflux, in a solution of LiAlH$_4$ (8.12 g, 214 mmol) in Et$_2$O (160 ml) under stirring. Then the mixture is further heated at reflux for 90 min. After cooling to 0-5° C., excess LiAlH$_4$ is neutralized by dropwise addition of H$_2$O (8 ml), 15% aqueous NaOH (8 ml) and H$_2$O (40 ml). The mixture is stirred until all LiAlH$_4$ is neutralized and a white precipitate is formed. The mixture is filtered and the precipitate is washed with Et$_2$O. The organic phase is dried (by granules of KOH) and is evaporated dry under reduced pressure to obtain an orange oil which is used with no other purification (11.78 g, 94%); $^1$H NMR (100 MHz, CDCl$_3$) δ: 0.74 (d, J=/Hz, 6H), 1.04 (m, 2H, H-3), 1.56 (m, J=7 Hz, 1H, H-4), 2.41 (m, 5H, H-1, 1 'OH, NH$_2$), 3.40 (m, J=4 Hz, 1H, H-2); $^{13}$C NMR (25 MHz, DMSO-d$_6$) δ: 21.90, 23.20, 24.30, 43.80, 47.80, 69.90. Analysis calculated for C$_6$H$_{15}$NO: C, 61.49; H, 12.90; N, 11.95. Experimental: C, 61.70; H, 12.53; N, 11.67.

1-Amino-4-phenylbutan-2-ol (1b)

1b is prepared from 2-hydroxy-4-phenylbutanenitrile according to the protocol described for 1a; LiAlH$_4$ (6.2 g, 163 mmol), Et$_2$O (120 ml), 2-hydroxy-4-phenylbutanenitrile (12.4 g, 77 mmol), H$_2$O (6.2 ml), 15% aqueous NaOH (6.2 ml) and H$_2$O (18 ml). The product, an orange oil, is used with no other purification (11 g, 87%); $^1$H NMR (100 MHz, CDCl$_3$) δ: 1.80 (m, 3H), 2.65 (m, 4H), 3.62 (m, 3H), 7.21 (s, 5H); $^{13}$C NMR (25 MHz, CDCl$_3$) δ: 33.98, 36.25, 70.92, 125.46, 128.04, 141.74. Analysis calculated for C$_{10}$H$_{15}$NO: C, 72.69; H, 9.15; N, 8.48. Experimental: C, 72.45; H, 9.33; N, 8.24.

1-[(3-Chloroquinoxalin-2-yl)amino]-4-methylpentan-2-ol (2a)

2,3-Dichloroquinoxaline (18.05 g, 90.7 mmol) is added to a solution of crude 1a (11.7 g, 99.8 mmol) and Et$_3$N (19 ml, 13.8 g, 136 mmol) in dioxane (210 ml). The solution obtained is heated at reflux (under N$_2$) for 6 h, it is then cooled to room temperature. Et$_3$N, HCl is eliminated by filtration and the filtrate is concentrated under reduced pressure. The dark orange residue is purified by chromatography on a silica column, eluent: CH$_2$Cl$_2$/MeOH (100:0→99:1), to obtain a yellow solid (12.14 g, 48%); $^1$H NMR (100 MHz, CDCl$_3$) δ: 0.72 (d, 3H), 0.78 (d, 3H), 1.60 (m, 3H), 3.68 (m, 4H), 5.82 (t, 1H), 7.58 (m, 4H); $^{13}$C NMR (25 MHz, CDCl$_3$) δ: 22.17, 23.35, 24.60, 44.32, 48.62, 69.67, 125.30, 125.62, 127.91, 130.36, 136.52, 137.92, 140.59, 148.62. Analysis calculated for C$_{14}$H$_{18}$N$_3$OCl: C, 60.10; H, 6.49; N, 15.02. Experimental: C, 59.87; H, 6.62; N, 15.25.

1-[(3-Chloroquinoxalin-2-yl)amino]-4-phenylbutan-2-ol (2b)

2b is obtained from 1b according to the protocol described for 2a; 2,3-dichloroquinoxaline (9.95 g, 50 mmol), 1b (9.02 g, 55 mmol) in dioxane (250 ml) with Et$_3$N (7.57 g, 75 mmol). The crude product is purified by chromatography on a silica column, eluent: CH$_2$Cl$_2$/MeOH (98:2) to obtain a yellow solid (10 g, 61%); $^1$H NMR (100 MHz, CDCl$_3$) δ: 1.76-1.97 (m, 2H), 2.70-2.90 (m, 2H), 3.53-4.05 (m, 4H), 5.96 (t, J=5 Hz, 1H), 7.23-7.82 (m, 9H). Analysis calculated for C$_{18}$H$_{18}$N$_3$OCl: C, 65.95; H, 5.53; N, 12.82. Experimental: C, 66.16; H, 5.43; N, 12.58.

1-[(3-Chloroquinoxalin-2-yl)amino]-4-methylpentan-2-one (3a)

A mixture of 2a (6.96 g, 24.8 mmol), 28.4 ml Et$_3$N and sulphur trioxide trimethylamine complex (7.9 g, 56.8 mmol) in 28.4 ml DMSO, is stirred overnight (under N$_2$) at room temperature, then ice water (50 ml) is added. The aqueous phase is extracted in CH$_2$Cl$_2$ (3×30 ml). The collected organic phases are dried (CaCl$_2$) and then evaporated under reduced pressure. The residues are purified by chromatography on a silica column, eluent: C$_6$H$_{12}$/Et$_2$O (85:15) to give a beige solid (4.18 g, 61%); $^1$H NMR (100 MHz, CDCl$_3$) δ: 0.93 (s, 3H), 1.00 (s, 3H), 2.34 (m, 1H), 2.40 (s, 2H), 4.38 (d, 2H), 6.39 (t, 1H), 7.59 (m, 4H); $^{13}$C NMR (25 MHz, CDCl$_3$) δ: 22.56, 25.01, 49.28, 51.55, 125.34, 125.87, 127.98, 130.14, 136.65, 137.92, 140.99, 147.30, 205.01. Analysis calculated for C$_{14}$H$_{16}$N$_3$OCl: C, 60.54; H, 5.81; N, 15.13. Experimental: C, 60.32; H, 6.06; N, 14.95.

1-[(3-Chloroquinoxalin-2-yl)amino]-4-phenylbutan-2-one (3b)

3b is prepared from 2b according to the protocol described for 3a; 2b (4.7 g, 14.4 mmol), 14.4 ml DMSO, 14.4 ml Et$_3$N, and Me$_3$N.SO$_3$ (4 g, 28.8 mmol). The product is purified by chromatography on a silica column, eluent: C$_6$H$_{12}$/Et$_2$O (80: 20) to give a yellow solid (4.51 g, 96%); $^1$H NMR (100 MHz, CDCl$_3$) δ: 2.82-3.01 (m, 4H), 4.38 (d, J=5 Hz, 2H), 6.4 (m, 1H), 7.23-7.84 (m, 9H). Analysis calculated for C$_{18}$H$_{16}$N$_3$OCl: C, 66.36; H, 4.95; N, 12.90. Experimental: C, 66.53; H, 5.23; N, 12.78.

4-Chloro-1-isobutylimidazo[1,2-a]quinoxaline (4a) (EAPB0101)

4a (16.39 g, 23 mmol) is solubilized in a mixture of trifluoroacetic anhydride (100 ml) and trifluoroacetic acid (1 ml), and stirred under nitrogen for 24 h at room temperature. The solvent is then evaporated under reduced pressure and the residue is solubilized in dichloromethane (300 ml). The organic phase is washed with 5% NaHCO$_3$ solution (75 ml) and then with water, dried by Na$_2$SO$_4$ and concentrated under a vacuum to give an orange oil. The product is purified by chromatography on a silica column, eluent C$_6$H$_{12}$/Et$_2$O (95: 5) to give a beige solid (5.04 g, 84%); $^1$H NMR (100 MHz, CDCl$_3$) d: 1.07 (d, J=6-7 Hz, 6H), 2.16 (m, 1H), 3.11 (d, J=6-7 Hz, 2H), 7.53-7.64 (m, 3H), 7.96-8.16 (m, 2H); $^{13}$C NMR (25 MHz, CDCl$_3$) d: 22.41, 26.88, 36.66, 115.39, 126.50, 128.41, 128.94, 130.04, 132.02, 134.37, 135.61, 136.60, 143.66. Analysis calculated for C$_{14}$H$_{14}$N$_3$Cl: C, 64.74; H, 5.43; N, 16.18. Found: C, 64.66; H, 5.55; N, 15.86.

4-Chloro-1-(2-phenylethyl)imidazo[1,2-a]quinoxaline (4b) (EAPB0201)

4b is prepared from 3b according to the protocol described for 4a; 3b (4 g, 12.2 mmol), trifluoroacetic anhydride (100 ml), trifluoroacetic acid (4 ml). The product is purified by chromatography on a silica column, eluent: CH$_2$Cl$_2$/MeOH (98:2) to give a yellow solid (2.5 g, 66%); $^1$H NMR (100 MHz, CDCl$_3$) δ: 3.20-3.31 (m, 2H), 3.53-3.68 (m, 2H), 7.32 (s, 5H), 7.54-7.63 (m, 3H), 7.99-8.31 (m, 2H); $^{13}$C NMR (25 MHz, CDCl$_3$) δ: 30.05, 33.80, 115.34, 126.54, 126.66, 128.19, 128.46, 128.70, 129.94, 129.20, 133.00, 139.72. Analysis calculated for C$_{18}$H$_{14}$N$_3$Cl: C, 70.24; H, 4.58; N, 13.65. Experimental: C, 70.04; H, 4.96; N, 13.82.

1-Isobutylimidazo[1,2-a]quinoxalin-4-amine (5a) (EAPB0102)

4a (1 g, 3.85 mmol) is heated at 120° C. for 4 h in the presence of an aqueous ammonia solution (60 ml at 30% (weight/volume), 0.5 mmol). The reaction mixture is cooled to room temperature and then filtered. The precipitate is washed with H$_2$O (10 ml), dissolved in CH$_2$Cl$_2$ (25 ml), and the organic phase is dried (Na$_2$SO$_4$) and then concentrated under reduced pressure. The crude product is purified by chromatography on a silica column, eluent: $CH_2Cl_2/MeOH$ (90:10) to give a yellow solid (0.75 g, 81%); $^1H$ NMR (100 MHz, DMSO-$d_6$) δ: 2.07 (m, J=6-7 Hz, 1H), 3.09 (d, J=6-7 Hz, 2H), 7.08-8.05 (m, 7H). Analysis calculated for $C_{14}H_{16}N_4$: C, 69.97; H, 6.71; N, 23.32. Experimental: C, 70.13; H, 6.97; N, 23.07.

1-(2-phenylethyl)imidazo[1,2-a]quinoxalin-4-amine (5b) (EAPB0202)

5b is prepared from 4b according to the protocol described for 5a; 4b (0.8 g, 2.6 mmol); aqueous ammonia solution (48 ml at 30% (weight/volume), 0.4 mmol). A yellow solid is obtained after purification by column chromatography as indicated for 5a (0.465 g, 62%); NMR (100 MHz, $CDCl_3$) δ: 3.10-3.24 (m, 2H), 3.48-3.63 (m, 2H), 5.74 (s, 2H), 7.20-7.48 (m, 8H), 7.69 (d, J=7.2 Hz, 1H), 8.05 (d, J=7.9 Hz, 1H); $^{13}C$ NMR (25 MHz, $CDCl_3$) δ: 29.75, 34.00, 115.01, 123.09, 125.94, 126.33, 126.78, 128.08, 128.46, 130.51, 130.89, 137.50, 140.04, 148.44. Analysis calculated for $C_{18}H_{16}N_4$: C, 74.98; H, 5.59; N, 19.43. Experimental: C, 74.86; H, 5.75; N, 19.37.

1-Isobutyl-N-methylimidazo[1,2-a]quinoxalin-4-amine (6a) (EAPB0103)

An aqueous solution of methylamine (0.6 ml at 40% (weight/volume), 6.93 mmol) is added dropwise to a solution of 4a (0.6 g, 2.31 mmol) in absolute EtOH (15 ml) at room temperature and under stirring. After 40 h, another portion of aqueous methylamine solution (0.6 ml at 40% (weight/volume), 6.93 mmol) is added and maintained under stirring for 3 additional hours. The solvent is evaporated under reduced pressure and the residue obtained is dissolved in $CH_2Cl_2$ (50 ml). The organic phase is successively washed with 5% $NaHCO_3$ (30 ml) and $H_2O$ (30 ml), dried ($Na_2SO_4$) and concentrated under reduced pressure. The product is purified by chromatography on a silica column, eluent: $C_6H_{12}$/EtOAc (70:30) to obtain a cream-coloured solid (0.49 g, 83%); $^1H$ NMR (100 MHz, $CDCl_3$) δ: 1.04 (d, J=6.2 Hz, 6H), 1.90-2.35 (m, 1H), 3.03 (d, J=7.0 Hz, 2H), 3.20 (d, J=4.9 Hz, 3H), 6.10-6.40 (m, 1H), 7.10-7.55 (m, 3H), 7.60-8.00 (m, 2H); $^{13}C$ NMR (25 MHz, $CDCl_3$) δ: 22.43, 26.93, 27.37, 36.65, 115.15, 122.49, 125.93, 126.63, 127.38, 130.43, 131.32, 134.01, 138.23, 148.41. Analysis calculated for $C_{15}H_{18}N_4$: C, 70.84; H, 7.13; N, 22.03. Experimental: C, 71.12; H, 7.44; N, 22.21.

N-methyl-1-(2-phenylethyl)imidazo[1,2-a]quinoxalin-4-amine (6b) (EAPB0203)

6b is prepared from 4b according to the protocol described for 6a; aqueous methylamine solution (0.260 ml at 40% (weight/volume), 3 mmol), 4b (0.307 g, 1 mmol). The crude product is purified by column chromatography, eluent: $CH_2Cl_2/MeOH$ (90:10) to obtain a yellow solid (0.2 g, 66%); $^1H$ NMR (100 MHz, $CDCl_3$) δ: 3.07-3.22 (m, 5H), 3.42-3.58 (m, 2H), 6.56 (d, J=5.6 Hz, 1H), 7.12-7.45 (m, 7H), 7.73 (d, J=9.1 Hz, 1H), 7.98 (d, J=7.9 Hz, 1H); $^{13}C$ NMR (25 MHz, $CDCl_3$) δ: 27.27, 29.76, 33.96, 114.93, 122.28, 125.79, 126.33, 127.05, 129.16, 129.49, 129.79, 130.51, 133.72, 133.97, 140.24, 149.14. Analysis calculated for $C_{19}H_{18}N_4$: C, 75.47; H, 6.00; N, 18.43. Experimental: C, 75.68; H, 6.15; N, 18.51.

1-Isobutyl-N,N-dimethylimidazo[1,2-a]quinoxalin-4-amine (7a) (EAPB0104)

7a is prepared from 4a according to the protocol described for 6a; aqueous dimethylamine solution (1.3 ml at 40% (weight/volume), 11.55 mmol), 4a (1.03 g, 3.85 mmol) in absolute EtOH (10 ml). The crude product is purified by chromatography on a silica column, eluent: $CH_2Cl_2/MeOH$ (97:3) to give a white solid (0.8 g, 78%); $^1H$ NMR (100 MHz, $CDCl_3$) δ: 1.03 (d, J=6-7 Hz, 6H), 2.16 (m, J=6-7 Hz, 1H), 3.03 (d, J=6-7 Hz, 2H), 3.58 (s, 6H), 7.15-7.41 (m, 3H), 7.62-7.72 (m, 1H), 7.86-7.95 (m, 9H); $^{13}C$ NMR (25 MHz, $CDCl_3$) δ: 22.42, 26.75, 36.89, 40.00, 114.86, 122.05, 125.80, 126.50, 126.80, 126.98, 129.51, 131.08, 134.74, 137.74, 149.15. Analysis calculated for $C_{16}H_{23}N_4$: C, 71.61; H, 7.51; N, 20.88. Experimental: C, 71.77; H, 7.23; N, 20.64.

N,N-Dimethyl-1-(2-phenylethyl)imidazo[1,2-a]quinoxalin-4-amine (7b) (EAPB0204)

7b is prepared from 4b according to the protocol described for 7a; 4b (0.32 g, 1 mmol), aqueous dimethylamine solution (0.44 ml at 40% (weight/volume), 3.90 mmol). The product is purified by column chromatography as indicated for 7a and a beige solid (0.2 g, 65%) is obtained; $^1H$ NMR (100 MHz, $CDCl_3$) δ: 3.09-3.26 (m, 2H), 3.42-3.54 (m, 2H), 3.59 (s, 6H), 7.14-7.42 (m, 8H), 7.70 (d, J=6.5 Hz, 1H), 8.00 (d, J=6.9 Hz, 1H); $^{13}C$ NMR (25 MHz, $CDCl_3$) δ: 30.41, 34.30, 40.12, 114.99, 125.25, 126.02, 126.58, 127.07, 128.43, 128.75, 129.89, 130.02, 134.84, 137.82, 140.57, 149.21. Analysis calculated for $C_{20}H_{20}N_4$: C, 75.92; H, 6.37; N, 17.71. Experimental: C, 75.82; H, 6.15; N, 17.57.

4-Methoxy-1-(2-phenylethyl)imidazo[1,2-a]quinoxaline (8b) (EAPB0206)

A methanol solution of sodium methylate was prepared from sodium (0.23 g, 10 mmol) and dry methanol (70 ml). 4b (1 g, mmol 4.9) was added and the resulting solution was heated at reflux for 2 h and was left under stirring for 24 h at room temperature. The reaction mixture was evaporated dry under vacuum and the residue was dissolved in dichloromethane (150 ml), washed with sodium chloride (100 ml), water (100 ml), and evaporated to give the crude product, which was purified by column chromatography, eluent: dichloromethane/methanol (98/2), to obtain the compound 8b (1.3 g, 95%); $^1H$ NMR (200 MHz, $CDCl_3$) δ: 8.77 (d, 1H, H1), 8.27 (dd, 1H, H9), 7.81 (dd, 1H, H6), 7.74 (d, 1H, H2), 7.56 (m, 2H, H7+H8), 4.15 (s, 3H, $OCH_3$). Analysis calculated for $C_{19}H_{17}N_3O$: C, 75.23; H, 5.65; N, 13.85. Experimental: C, 75.19; H, 5.69; N, 13.88.

Diimidazo[1,2-a;1',2'-d]pyrazine-5,10-dione (9)

2-Imidazocarboxylic acid (2.5 g, 22.3 mmol) suspended in thionyl chloride (40 ml). The mixture is brought to reflux, under stirring for 18 h. A milky orange-brown mixture is obtained. The reaction medium is cooled, then filtered on frit. The yellow solid thus obtained is washed with toluene and then dried under vacuum (3.52 g, 84.4%); $^1H$ NMR (300 MHz, DMSO-$d_6$) δ: 8.1 (s, 2H, ArH); 7.45 (s, 2H, ArH). Analysis calculated for $C_8H_4N_4O_2$: C, 51.07; H, 2.14; N, 29.78. Experimental: C, 51.15; H, 2.21; N, 29.46.

N-(2-Fluorophenyl)-1H-imidazol-2-carboxamide (10)

Ortho-fluoroaniline (1.91 ml, 19.77 mmol) is mixed with a solution of anhydrous THF (13 ml) at −10° C., then a solution of sodium bis(trimethylsilyl)amide (NaHMDS) (45.2 ml, 45.2 mmol in 1 M THF) is introduced. The mixture is left under stirring for 1 h at −10° C.; a suspension of 9 (1.77 g, 9.4 mmol) in anhydrous THF (20 ml) is then added, and the mixture obtained is left under stirring at room temperature for approximately 3 h. To quench the reaction, acetic acid solution is introduced dropwise. A brick red precipitate is formed. The solvent is evaporated under vacuum, and then to the dry residue are added water and a saturated aqueous sodium bicarbonate solution. A brownish-red precipitate then appears and is recovered by filtration. The solid obtained is washed with water and then hexane, and then dried under vacuum. A brown solid is obtained (3.24 g, 80%); $^1$H NMR (300 MHz, DMSO-$d_6$) δ: 8.12 (dd, 1H, ArH), 7.92 (dd, 1H, ArH), 6.92 (t, 1H, ArH), 7.13 (t, 1H, ArH), 7.07 (s, 2H, CH—CH). Analysis calculated for $C_{10}H_8FN_3O$: C, 58.54; H, 3.93; N, 20.48. Experimental: C, 58.33; H, 3.55; N, 20.14.

5H-Imidazo[1,2-a]quinoxalin-4-one (11)

10 (2 g, 9.75 mmol) is solubilized in N,N-dimethylacetamide (DMA) (80 ml) before adding sodium hydride (NaH 60% by weight) (1.5 g, 62 mmol). The mixture thus obtained is carried at reflux for 15 h. The reaction is monitored by TLC, eluent: MeOH/$CH_2Cl_2$ (10/90). This not being complete, 2 equivalents of NaH are added. The mixture is left at reflux for 30 h. Once the reaction is complete, the mixture is concentrated under vacuum, then to the dry residue are added water and a saturated ammonium chloride aqueous solution. A brown precipitate is formed, which is collected by filtration, washed with water and dried under vacuum. A beige solid (1.42 g, 79%) is obtained. Analysis calculated for $C_{10}H_7N_3O$: C, 64.86; H, 3.81; N, 22.69. Experimental: C, 64.44; H, 4.03; N, 22.98.

4-Chloroimidazo[1,2-a]quinoxaline (12)

Compound 11 (1.4 g, 6.4 mmol) is solubilized in phosphorus oxychloride (24 ml), and N,N-diethylaniline (3.6 ml). The reaction mixture obtained is carried to reflux for approximately 2 h. The product is insoluble in $POCl_3$ even after heating. The reaction is monitored by TLC, eluent: $CH_2Cl_2$/MeOH (95/5). TLC shows the presence of the end product, but also the appearance of breakdown products. The reaction mixture is dark brown in colour. The $POCl_3$ is evaporated under vacuum. The residue is cooled in an ice bath before adding a little water and, dropwise, a saturated sodium bicarbonate solution to neutralize $POCl_3$. A light yellow foam and a brown precipitate appear. The solid is isolated by filtration and is recrystallized in methanol. A beige solid (0.97 g, 75%) is obtained; $^1$H NMR (300 MHz, DMSO-$d_6$) δ: 8.5 (s, 1H, N—CH—C), 8.06 (d, 1H, ArH), 7.56 (s, 1H, C—CH—N), 7.35 (m, 1H, ArH), 7.25 (m, 2H, ArH). Analysis calculated for $C_{10}H_6N_3Cl$: C, 58.98; H, 2.97; N, 20.64. Experimental: C, 59.12; H, 2.76; N, 20.45.

N-Methylimidazo[1,2-a]quinoxalin-4-amine (13)

Compound 12 (0.110 g, 0.54 mmol) is solubilized in EtOH (10 ml), and then a solution of methylamine in water (40% by weight) (0.15 ml, 1.74 mmol) is introduced. The mixture is left under stirring in an autoclave, at room temperature, for at least 15 h. The product, initially insoluble, is solubilized shortly thereafter. The progression of the reaction is controlled by TLC, eluent: $CH_2Cl_2$/MeOH (95/5). At the end of 15 h, 1.5 eq (0.06 ml) of methylamine are added. After 5 h of stirring, the reaction progresses no further. The solvent is evaporated dry under vacuum. The yellowish residue obtained is solubilized in dichloromethane (10 ml). This organic phase is washed using a saturated sodium bicarbonate solution (10 ml) and then water (10 ml). It is then dried on $Na_2SO_4$ and then evaporated under vacuum. A white solid is recovered. The residue is purified on a silica gel column in order to eliminate traces of the starting product, eluent: $CH_2Cl_2$/AcEt (70/30). A white solid (0.99 g, 93%) is obtained; $^1$H NMR (300 MHz, DMSO-$d_6$) δ: 7.92 (s, 1H, C—CH—N), 7.75 (dd, J1=1.22 Hz, J2=8.17 Hz, 1H, ArH), 7.65 (dd, J1=1.26 Hz, J2=8.06 Hz, 1H, ArH), 7.52 (s, 1H, N—CH—C), 7.4 (t, 1H, ArH), 7.25 (t, 1H, ArH), 6.15 (s, 1H, NH), 3.25 (d, 3H, —$CH_3$); $^{13}$C NMR (200 MHz, DMSO-$d_6$) δ: 142.25, 139.17, 131.99, 129.40, 128.17, 127.20, 125.14, 124.34, 114.14, 113.89, 29.20. Analysis calculated for $C_{11}H_{10}N_4$: C, 66.65; H, 5.08; N, 28.26. Experimental: C, 66.26; H, 5.53; N, 28.23.

1-Bromo-N-methylimidazo[1,2-a]quinoxalin-4-amine (14)

A solution of 13 (1.5 g, 7.5 mmol) and of N-bromosuccinimide (1.5 g, 7.5 mmol) in chloroform is heated at reflux for 2 h. The resulting reaction mixture is cooled, washed with a 5% solution of sodium hydrogenocarbonate, dried with sodium sulphate, and evaporated under vacuum. The residue is purified on a silica gel column, eluent: $CH_2Cl_2$/MeOH (85/1). A white solid (1.18 g, 57%) is obtained; $^1$H NMR (300 MHz, DMSO-$d_6$) δ: 9.10 (s, 1H, C—CH—N), 7.75 (dd, 1H, ArH), 7.65 (dd, 1H, ArH), 7.4 (t, 1H, ArH), 7.25 (t, 1H, ArH), 6.15 (s, 1H, NH), 3.25 (d, 3H, —$CH_3$). Analysis calculated for $C_{11}H_9N_4Br$: C, 47.68; H, 3.27; N, 20.22. Experimental: C, 47.33; H, 3.53; N, 20.53.

General Procedure for the Suzuki Reaction:

To a mixture of 14 (300 mg, 1.08 mmol) and tetrakis (63 mg, 0.05 mmol) in DME (15 ml) is added the corresponding boronic aryl acid followed by sodium carbonate (234 mg) in water (5 ml). The reaction is irradiated under microwave in a sealed tube at 140° C. for 20 min in a Biotage synthesizer. The reaction is poured into water and extracted by dichloromethane (2×40 ml). The organic phases are washed with water (40 ml), dried and concentrated dry under vacuum. The crude product is purified by column chromatography (silica gel using dichloromethane as eluent).

N-methyl-1-phenylimidazo[1,2-a]quinoxalin-4-amine (15a) (EAPB0403)

Phenylboronic Acid (260 mg, 2.13 mmol). White Solid (90%); $^1$H NMR (300 MHz, CDCl$_3$-$d_6$) δ: 8.15 (s, 1H), 7.99 (dd, 1H), 7.52 (m, 8H), 5.7 (s, 1H), 3.01 (d, 3H). Analysis calculated for $C_{17}H_{14}N_4$: C, 74.43; H, 5.14; N, 20.42. Experimental: C, 74.15; H, 5.46; N, 20.09.

1-(3-methoxyphenyl)-N-methylimidazo[1,2-a]quinoxalin-4-amine (15b) (EAPB0503)

3-Methoxyphenylboronic acid (329 mg, 2.16 mmol). White solid (90%); $^1$H NMR (300 MHz, CDCl$_3$-$d_6$) δ: 9.04 (s, 1H), 8 (dd, 1H), 7.82 (m, 2H), 7.4 (m, 3H), 6.99 (d, 1H), 6.86 (s, 1H), 5.7 (s, 1H), 3.83 (s, 3H), 2.88 (d, 3H). Analysis calculated for $C_{18}H_{16}N_4O$: C, 71.04; H, 5.30; N, 18.41. Experimental: C, 71.40; H, 5.66; N, 18.09.

1-(4-methoxyphenyl)-N-methylimidazo[1,2-a]quinoxalin-4-amine (15c) (EAPB0703)

4-Methoxyphenylboronic acid (329 mg, 2.16 mmol). White solid (95%). $^1$H NMR (300 MHz, CDCl$_3$-$d_6$) δ: 8.14 (s, 1H), 8.00 (d, 1H), 7.67 (m, 3H), 7.5 (m, 2H), 7.05 (m, 2H), 5.77 (s, 1H), 3.82 (s, 3H), 2.99 (s, 3H). Analysis calculated for C$_{18}$H$_{16}$N$_{4}$O: C, 71.04; H, 5.30; N, 18.41. Experimental: C, 71.18; H, 5.58; N, 18.13.

1-(2-methoxyphenyl)-N-methylimidazo[1,2-a]quinoxalin-4-amine (15d) (EAPB0803)

2-Methoxyphenylboronic acid (329 mg, 2.16 mmol). Beige solid (94%). $^1$H NMR (300 MHz, CDCl$_3$-d$_6$) δ: 8.1 (d, 1H), 7.60 (m, 3H), 7.48 (t, 1H), 7.30 (m, 4H), 5.74 (s, 1H), 3.85 (s, 3H), 3.00 (s, 3H). Analysis calculated for C$_{18}$H$_{16}$N$_{4}$O: C, 71.04; H, 5.30; N, 18.41. Experimental: C, 70.98; H, 5.12; N, 18.22.

1-(3-ethoxyphenyl)-N-methylimidazo[1,2-a]quinoxalin-4-amine (15e) (EAPB0903)

3-Ethoxyphenylboronic acid (360 mg, 2.17 mmol). White solid (52%). $^1$H NMR (300 MHz, CDCl$_3$-d$_6$) δ: 8.34 (s, 1H), 8.02 (d, 1H), 7.83 (d, 1H), 7.67 (t, 1H), 7.5 (m, 2H), 6.96 (d, 1H), 6.85 (s, 1H), 5.74 (s, 1H), 3.89 (m, 2H), 2.89 (s, 3H), 1.38 (t, 3H). Analysis calculated for C$_{19}$H$_{17}$N$_{4}$O: C, 71.92; H, 5.36; N, 17.67. Experimental: C, 72.13; H, 5.56; N, 17.59.

1-(3-hydroxyphenyl)-N-methylimidazo[1,2-a]quinoxalin-4-amine (15f) (EAPB0603)

3-Hydroxyphenylboronic acid (329 mg, 2.16 mmol). White solid (85%). $^1$H NMR (300 MHz, CDCl$_3$-d$_6$) δ: 8.33 (s, 1H), 7.99 (d, 1H), 7.79 (d, 1H), 7.70 (m, 2H), 7.67 (t, 1H), 7.50 (m, 3H), 6.857 (m, 2H), 3.02 (s, 3H). Analysis calculated for C$_{17}$H$_{15}$N$_{4}$O: C, 70.09; H, 5.19; N, 19.23. Found: C, 70.49; H, 5.28; N, 19.09.

1-(3-bromophenyl)-N-methylimidazo[1,2-a]quinoxalin-4-amine (15 g) (EAPB01003)

3-Bromophenylboronic acid (435 mg, 2.16 mmol). Yellow solid (78%). $^1$H NMR (300 MHz, CDCl$_3$-d$_6$) δ: 8.18 (s, 1H), 7.90 (m, 2H), 7.67 (t, 1H), 7.50 (m, 2H), 7.45 (m, 3H), 5.74 (s, 1H), 2.98 (s, 3H). Analysis calculated for C$_{17}$H$_{13}$BrN$_{4}$: C, 57.81; H, 3.71; N, 15.86. Experimental: C, 58.05; H, 3.55; N, 15.99.

1-(3-(trifluoromethyl)-phenyl))-N-methylimidazo[1,2-a]quinoxalin-4-amine (15h) (EAPB01103)

3-(Trifluoromethyl)-phenylboronic acid (411 mg, 2.16 mmol). White solid (98%). $^1$H NMR (300 MHz, CDCl$_3$-d$_5$) δ: 8.14 (s, 1H), 8.10 (s, 1H), 8.02 (m, 2H), 7.85 (d, 1H), 7.60 (m, 2H), 7.48 (t, 1H), 5.74 (s, 1H), 2.96 (s, 3H). Analysis calculated for C$_{18}$H$_{12}$N$_{4}$F$_{3}$: C, 63.34; H, 3.52; N, 16.42. Experimental: C, 63.03; H, 3.86; N, 16.74.

1-(3-chlorophenyl)-N-methylimidazo[1,2-a]quinoxalin-4-amine (15i) (EAPB01203)

3-Chlorophenylboronic acid (339 mg, 2.16 mmol). Yellow solid (63%). $^1$H NMR (300 MHz, CDCl$_3$-d$_6$) δ: 8.48 (s, 1H), 8.02 (d, 1H), 7.67 (t, 1H), 7.58 (m, 2H), 7.49 (m, 3H), 7.10 (s, 1H), 5.74 (s, 1H), 2.81 (s, 3H). Analysis calculated for C$_{17}$H$_{13}$ClN$_{4}$: C, 66.13; H, 4.24; N, 11.48. Experimental: C, 66.35; H, 4.01; N, 11.25.

1-(3-carboxyphenyl)-N-methylimidazo[1,2-a]quinoxalin-4-amine (15j) (EAPB01303)

3-Carboxyphenylboronic acid (357 mg, 2.16 mmol). Orange solid (87%). $^1$H NMR (300 MHz, CDCl$_3$-d$_6$) δ: 8.41 (d, 1H), 8.26 (s, 1H), 8.01 (m, 2H), 7.80 (m, 4H), 7.58 (m, 2H), 7.47 (t, 1H), 2.95 (s, 3H). Analysis calculated for C$_{18}$H$_{14}$N$_{4}$O$_{2}$: C, 67.92; H, 4.43; N, 17.60. Experimental: C, 67.72; H, 4.35; N, 17.63.

1-(3-fluorophenyl)-N-methylimidazo[1,2-a]quinoxalin-4-amine (15k) (EAPB01403)

3-Fluorophenylboronic acid (303 mg, 2.16 mmol). Yellow solid (66%). $^1$H NMR (300 MHz, CDCl$_3$-d$_6$) δ: 8.22 (s, 1H), 7.98 (d, 1H), 7.59 (m, 3H), 7.48 (m, 2H), 7.22 (s, 1H), 7.03 (d, 1H), 5.74 (s, 1H), 2.96 (s, 1H). Analysis calculated for C$_{17}$H$_{13}$FN$_{4}$: C, 69.85; H, 4.48; N, 19.17. Experimental: C, 69.79; H, 4.48; N, 18.97.

1-(3-cyanophenyl)-N-methylimidazo[1,2-a]quinoxalin-4-amine (15l) (EAPB01503)

3-Cyanophenylboronic acid (351 mg, 2.16 mmol). Beige solid (84%). $^1$H NMR (300 MHz, CDCl$_3$-d$_5$) δ: 8.41 (s, 1H), 8.13 (d, 1H), 8.00 (d, 1H), 7.77 (d, 1H), 7.64 (m, 3H), 7.51 (m, 2H), 5.77 (s, 1H), 2.76 (s, 3H). Analysis calculated for C$_{17}$H$_{13}$N$_{5}$: C, 72.23; H, 4.38; N, 23.40. Experimental: C, 72.01; H, 4.71; N, 23.25.

1-(3-nitrophenyl)-N-methylimidazo[1,2-a]quinoxalin-4-amine (15m) (EAPB01603)

3-Nitrophenylboronic acid (399 mg, 2.16 mmol). Beige solid (95%). $^1$H NMR (300 MHz, CDCl$_3$-d$_6$) δ: 8.21 (s, 1H), 8.01 (d, 1H), 7.70 (m, 2H), 7.58 (d, 1H), 7.40 (m, 2H), 7.17 (m, 2H), 5.17 (s, 1H), 3.01 (s, 3H). Analysis calculated for C$_{17}$H$_{13}$N$_{5}$O: C, 63.94; H, 4.10; N, 31.93. Experimental: C, 64.13; H, 3.89; N, 21.66.

1-furan-N-methylimidazo[1,2-a]quinoxalin-4-amine (15n) (EAPB01703)

Furanboronic acid (243 mg, 2.16 mmol). White solid (96). $^1$H NMR (300 MHz, CDCl$_3$-d$_6$) δ: 8.24 (s, 1H), 7.90 (m, 3H), 7.83 (s, 1H), 7.62 (t, 1H), 7.50 (m, 2H), 7.12 (m, 2H), 6.98 (s, 1H), 5.74 (s, 1H), 4.85 (d, 1H), 2.85 (s, 3H). Analysis calculated for C$_{15}$H$_{16}$N$_{4}$O: C, 68.17; H, 4.58; N, 21.20. Experimental: C, 68.20; H, 4.56; N, 21.17.

2) Studies on Melanoma

Study of In Vitro Cytotoxicity

Antiproliferative activity was first measured on a cancer cell line of human origin, A375 melanoma. Later, cytotoxicity tests were conducted for the most active molecules on other melanoma cancer lines as well as on colon, breast, ovary and B lymphoma cancer lines.

Imiquimod and fotemustine (Muphoran®) are used as controls in this study.

Several human carcinoma cell lines were used:
Lines A375, M4Be, RPMI7591 from human melanoma.
Line LS174T from colon carcinoma.
Line A 2780 from ovarian carcinoma.
The Raji line from B lymphoma.
Line MCF7 from breast carcinoma.

IC$_{50}$ (concentration of the product tested which inhibits 50% of the maximum cell proliferation observed in the control wells) is determined graphically from the curve of the percentage of cell proliferation as a function of concentration of the product tested.

a) Results of In Vitro Cytotoxicity Studies

The $IC_{50}$ and standard deviation of each product tested in vitro on the A375 melanoma line are presented in Table 1. The compounds tested have the following structure:

TABLE 1

Structures of compounds and their cytotoxic activity in vitro.

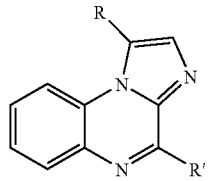

| Compound | R | R' | $IC_{50}$ (μM) |
| --- | --- | --- | --- |
| EAPB0103 | $(CH_3)_2$—CH—$CH_2$— | $CH_3$—NH— | 31.6 ± 2.0 |
| EAPB0203 | $C_6H_5$—$(CH_2)_2$— | $CH_3$—NH— | 1.57 ± 0.56 |
| EAPB0202 | $C_6H_5$—$(CH_2)_2$— | $NH_2$— | 2.35 ± 0.15 |
| EAPB0201 | $C_6H_5$—$(CH_2)_2$— | Cl— | 24.0 ± 0.5 |
| EAPB0104 | $(CH_3)_2$—CH—$CH_2$— | $(CH_3)_2$—N— | 66.3 ± 7.5 |
| EAPB0204 | $C_6H_5$—$(CH_2)_2$— | $(CH_3)_2$—N— | 80.1 ± 7.0 |
| EAPB0206 | $C_6H_5$—$(CH_2)_2$— | $CH_3$—O— | 47.8 ± 5.0 |

Comparison of $IC_{50}$ values reveals two very active molecules among the compounds tested, namely EAPB0203 ($IC_{50}$=1.57 μM) and EAPB0202 ($IC_{50}$=2.35 μM). Indeed, EAPB0203, which corresponds to our "lead" compound, has an activity 110 times higher than that of fotemustine and 50 times higher than that of imiquimod. EAPB0202 exhibits activity very close to EAPB0203 (almost 2 times more active than EAPB0204) with an $IC_{50}$ 70 times higher than fotemustine and 30 times higher than imiquimod. The other compounds have an $IC_{50}$ which varies between 20 and 100 μM. The $IC_{50}$ of fotemustine and imiquimod are presented in Table 2.

Then our "lead" compound EAPB0203 was tested on other human melanoma cell lines (M4Be and RPMI7591), LS174T (colon cancer), MCF7 (breast cancer), and Raji (B lymphoma) to observe its possible activity by comparing it to imiquimod and to the appropriate reference molecules for each type of cancer.

The $IC_{50}$ values are presented in Table 2.

other molecules, which were evaluated in vitro on A375. The $IC_{50}$ values are presented in Table 3 in comparison with EAPB0203.

TABLE 3

Structures of the compounds and their cytotoxic activity in vitro.

| Compound | R | Formula | $IC_{50}$ (μM) |
| --- | --- | --- | --- |
| 15a (EAPB0403) | $C_6H_5$— | $C_{18}H_{16}N_4O$ | 2.19 ± 0.08 |
| 15b (EAPB0503) | 3-$OCH_3$—$C_6H_5$— | $C_{18}H_{16}N_4O$ | 0.18 ± 0.09 |
| 15c (EAPB0703) | 4-$OCH_3$—$C_6H_5$— | $C_{18}H_{16}N_4O$ | 0.37 ± 0.4 |
| 15d (EAPB0803) | 2-$OCH_3$—$C_6H_5$— | $C_{18}H_{16}N_4O$ | 122 ± 25 |
| 15e (EAPB0903) | 3-$OC_2H_5$—$C_6H_5$— | $C_{19}H_{17}N_4O$ | 0.30 ± 0.01 |
| 15f (EAPB0603) | 3-OH—$C_6H_5$— | $C_{17}H_{15}N_4O$ | 0.56 ± 0.12 |
| 15g (EAPB01003) | 3-Br—$C_6H_5$— | $C_{17}H_{13}BrN_4$ | 0.65 ± 0.02 |
| 15h (EAPB01103) | 3-$CF_3$—$C_6H_5$— | $C_{18}H_{12}N_4F_3$ | 1.28 ± 0.18 |
| 15i (EAPB01203) | 3-Cl—$C_6H_5$— | $C_{17}H_{13}ClN_4$ | 1.78 ± 0.35 |
| 15j (EAPB01303) | 3-COOH—$C_6H_5$— | $C_{18}H_{14}N_4O_2$ | 3.47 ± 0.55 |
| 15k (EAPB01403) | 3-F—$C_6H_5$— | $C_{17}H_{13}FN_4$ | 24.9 ± 0.27 |
| 15l (EAPB01503) | 3-CN—$C_6H_5$— | $C_{18}H_{13}N_5$ | 27.0 ± 2.2 |
| 15m (EAPB01603) | 3-$NO_2$—$C_6H_5$— | $C_{17}H_{13}N_5O$ | 40.0 ± 3.9 |
| 15n (EAPB01703) | $(C_4H_3O)$— | $C_{15}H_{16}N_4O$ | 74.1 ± 3.1 |
| EAPB0203 | $C_6H_5$—$(CH_2)_2$— | $C_{19}H_{18}N_4$ | 1.57 ± 5.6 |

The substitution of EAPB0203 by various aryl groups in position R and by a methylamine in position R' (Table 3) made it possible to obtain a library of compounds. By comparing $IC_{50}$ values one finds that some of these promising compounds (15b, 15c, 15th, 15f, 15 g) exhibit activities that are higher than that of EAPB0203. Moreover, all the compounds tested exhibit an activity higher than that of fotemustine and imiquimod, used as references.

Very recently, new compounds with substitution R in position 2 instead of position 1 on the imidazol ring as for the preceding compounds clearly show improved anti-cancer activity on melanoma (A375). Indeed, for example, the compound corresponding to EAPB0503 with substitution of 3-methoxyphenyl in position 2 exhibits activity 10 times higher ($IC_{50}$=0.018 μM) than that of EAPB0503 and 100 times higher than EAPB0203.

Study of the Anti-Proliferative Activity of EAPB0203 In Vivo (Melanoma)

In this study, data are presented relating to the activity of EAPB0203 on the volume of a type of human melanoma

TABLE 2

$IC_{50}$ values of imiquimod, fotemustine, methothrexate, irinotecan, doxorubicin and EAPB0203 on A35, M4Be and RMPI 7590 (melanoma), LS174T (colon cancer), MCF7 (breast cancer), Raji (B lymphoma).

| | $IC_{50}$ | | | | | |
| --- | --- | --- | --- | --- | --- | --- |
| Compounds | A375 | M4Be | RPMI7591 | MCF7 | LS174T | Raji |
| Fotemustine | 173 ± 24 | 326 ± 34 | 125 ± 49 | | | |
| Doxorubicine | | | | 0.13 ± 0.01 | | |
| Irinotecan | | | | | 1.16 ± 0.07 | |
| Methothrexate | | | | | | 0.04 ± 0.005 |
| Imiquimod | 70.3 ± 4.3 | 33.5 ± 7.7 | 53.7 ± 9.8 | 145 ± 7 | 34.4 ± 9.7 | 139 ± 12 |
| EAPB0203 | 1.57 ± 0.56 | 2.58 ± 0.40 | 4.23 ± 0.48 | 1.08 ± 0.46 | 4.12 ± 0.67 | 6.23 ± 0.06 |

It is concluded that EAPB0203 exhibits activities on the order of μM on the various cancer cell lines tested with significant activity on melanoma compared to that of the reference molecule, fotemustine.

Application of the second synthesis strategy on the imidazo[1,2-a]quinoxaline series made it possible to synthesize tumour model (M4Be lines), xenografted in athymic mice. This study required as a preliminary step several tests of grafts of human melanoma cell lines in athymic mice before establishing the adequate animal model. The in vivo study was performed following the in vitro experiments described previously.

a) Determination of the Lethal Dose 50 ($LD_{50}$) of EAB0203 in the Mouse

The $LD_{50}$ of EAPB0203 was determined by using three doses: 30 mg/kg, 300 mg/kg, and 450 mg/kg. After 48 h, EAPB0203 at the highest doses did not display any apparent toxicity. It thus does not show any acute toxicity ($LD_{50}>450$ mg/kg) in the mouse.

b) Activity of EAPB0203 in Vivo

EAPB0203 induces significant cytotoxicity in vitro in human melanoma cells, in particular M4Be. The activity and specificity of EAPB0203 in vivo on tumour growth of human melanoma are evaluated by monitoring tumour development in mice carrying M4Be melanoma treated by administration of fotemustine and EAPB0203 at various doses.

For this study, 18 Swiss nude mice (3 groups of 6 mice) were used. M4Be cancer cells in suspension were injected subcutaneously into the right flank of each athymic Swiss nude female 7-week-old mouse weighing 20-22 g at the beginning of the protocol. The mice were then maintained in a sterile atmosphere and received aseptic food and water. The weight of the mouse and the growth of the tumour in three dimensions were recorded twice a week.

A first group of 6 mice (reference) will receive fotemustine by intra-peritoneal route at a dose of 20 mg/kg once per week for 3 weeks, beginning 7 days after inoculation at the time when the tumour will be visible and palpable. A second group of 6 mice will receive EAPB0203 at the same dose of 20 mg/kg via intra-peritoneal route but twice per week (40 mg/kg per week). The third group (control) of 6 mice will receive only the administration carrier. Tumour volume is calculated by the following formula: length X width X height X 0.52, and is expressed as mean±SEM $mm^3$.

For fotemustine and EAPB0203, the sequence of administrations is a treatment of three weeks, then two weeks without treatment, and then a second treatment of three weeks.

EAPB0203 (20 mg/kg twice per week) was well tolerated without loss of weight or apparent side effects. The mice treated with EAPB0203 exhibited a significant delay in tumour growth compared to that of the control mice and the fotemustine mice (FIG. 1). In the control group, the last mice were sacrificed on day 55, with tumour volume having reached 2 $cm^3$. In the fotemustine group the last mice were euthanatized on day 76 whereas in the EAPB0203 group a mouse still had a tumour volume less than 2 $cm^3$.

c) Pharmacokinetic Study

Methods of assaying compounds EAPB0203, EAPB0503 and EAPB0603 by high performance liquid chromatography and detection by mass spectrometry (LC/ESI-MS) were developed and validated in human and rat plasmas. Pre-treatment of the samples consists of a liquid solid extraction preceded by precipitation of plasma proteins in acid medium. The chromatographic column used is C8 Zorbax eclipse XDB and the mobile phase (gradient) a mixture of acetonitrile and formate buffer (pH 3) (flow rate, 0.8 ml/min). The accuracy of the methods developed is $\leq 14\%$ and the precision varies from 92 to 113%. The extraction coefficients are higher than 72%. The quantification limit is 5 µg/l for all analytes. Stability tests of the compounds in the matrices were also carried out. These methods were used to determine the pharmacokinetic parameters of compounds EAPB0203, EAPB0503 and EAPB0603 in the rat. The lethal doses 50% of compounds EAPB0203 and EAPB0503 are respectively 14.8 and 7.6 mg/kg. In the rat, compound EAPB0603 is the active metabolite of EAPB0503. After intravenous administration of EAPB0503 at a dose of 5 mg/kg, the pharmacokinetic parameters are as follows: i) EAPB0503: total clearance, 2.2 l/h/kg; volume of distribution at equilibrium, 5.6 l/kg; area under the curve of plasma concentrations, 2.31 mg×h/l and elimination half-life, 1.76 h: ii) EAPB0603: area under the curve of plasma concentrations, 0.439 mg×h/l and elimination half-life, 4.7 h; and EAPB0203: total clearance, 2.9 l/h/kg; volume of distribution at equilibrium, 10.6 l/kg; area under the curve of plasma concentrations, 0.87 mg×h/l and elimination half-life, 2.6 h.

D) Semichronic Toxicity of Compounds EAPB0503 and EAPB0203 in the Rat

The animals were divided randomly into four groups:
group 1: 5 animals receive EAPB0203 by intravenous route at a dose of 5 mg/kg, once per day for 5 days,
group 2: 5 animals receive EAPB0503 by intravenous route at a dose of 3 mg/kg, once per day for 5 days,
group 3: 3 animals receive the carrier (100 µl DMSO) once per day for 5 days,
group 4: 3 animals are not treated and are used as controls.

The compounds studied being insoluble in aqueous medium, they are solubilized in 100 µl DMSO and then administered in the tail vein.

Clinical follow-up: a clinical examination of each rat is performed twice a day in order to note any signs of toxicity or change of behaviour. Weight is measured each day as well as the consumption of water and food.

Hematologic tests: in order to evaluate possible hematologic toxicity of the compounds studied, 0.5 ml of blood was taken by cardiac puncture in tubes containing EDTA, before the beginning of the treatment and then 4 and 7 days afterwards. The following hematologic tests were performed:
red blood cell count,
platelet count,
white blood cell count,
haemoglobin level,
haematocrit.

After 7 days, the animals are euthanized with sevoflurane and a macroscopic examination of the principal organs (liver, kidney, spleen, lungs, heart and brain) is carried out. The organs were then removed for anatomopathological examination. The treatment was well tolerated by all the animals. Weight gain and consumption of water and food were comparable between treated animals and control animals. No haematological toxicity was observed. Macroscopic examination of the organs did not reveal any anomaly; anatomopathological examination is underway.

3) Studies on T-Cell Lymphomas

The in vitro activity of EAPB0203 on adult T-cell leukemia (ATL) transformed by retrovirus HTLV-I (HuT-102, MT2 . . . ) and malignant HTLV-I-negative T-cells (CEM, Jurkatt . . . ) was evaluated. Initially, the effect of EAPB0203 on cell growth of these lines was evaluated by two techniques, the nonradioactive "CellTiter 96®" cell growth kit and the trypan blue exclusion method. Concentrations of EAPB0203, from 1 to 10 µM, had as a consequence a progressive, dose-dependent inhibition on the growth of ATL cells and malignant T-cells not associated with HTLV-I. EAPB0203 also induced inhibition of cell proliferation of new leukaemic cells derived from two patients with ATL. On the other hand, normal lymphocytes activated or not activated by PHA from two healthy subjects were completely resistant to EAPB0203 (FIG. 2).

The mechanisms of inhibition of cell proliferation caused by EAPB0203 in the cell lines studied were determined by flow cytometry. This study evaluated the distribution of cells in the various phases of the cell cycle. For treated cells, a progressive accumulation of cells in phase G2 was observed whereas the number of cells decreased in phase G1. Analysis of the cell cycle also highlights the presence of a pre-G0/G1 apoptotic population in the various treated cell lines. This pre-G0/G1 peak corresponds to cells whose DNA content is decreased by loss of cleaved DNA fragments during cell death (FIG. 3).

Determination of the mechanism of action was studied on the basis of the assumption that imiquimod induces cell death by apoptosis via the intrinsic mitochondrial route. A study of apoptosis by double labelling, namely membrane labelling with Annexin-V conjugated to FITC and nuclear labelling with propidium iodide (PI), followed by analysis by fluorescence microscopy was carried out. Apoptotic cells showing externalisation of phosphatidylserine (PS) were labelled with AnnexinV+ but remain PI−, whereas dead cells are PI+. Analysis by fluorescence microscopy made it possible to determine the percentage of cells in apoptosis after treatment. A similar experiment was also carried out with the labelling of chromatin in Hoechst 33342. This enables evaluation of the percentage of the condensation of chromatin, which is an index of apoptosis.

Mitochondria play a central role in apoptotic mechanisms. The first detectable cellular disturbance during the apoptotic process is a reduction in mitochondrial transmembrane potential.

This reduction was demonstrated using Rhodamine 123 dye followed by flow cytometry of cells in suspension.

Sub-cellular localization of cytochrome C in the treated cell lines reveals the presence of cytochrome C in the cytoplasm after treatment by EAPB0203, indicating a salting out of cytochrome C by mitochondria during apoptosis.

The apoptosis observed is studied in order to know if it is due or not to the activation of caspases. Proteinic cell extracts were obtained after various treatments and evaluation of the expression of certain proteins was studied by western blot. Indeed, in CEM and HuT-102 cells, apoptosis induced by EAPB0203 was associated with the activation of caspases, as the cleavage of PARP shows, and of procaspase-3, procaspase-8, and procaspase-9 in their activated forms. Moreover, co-treatment by caspase inhibitor zVAD enabled partial protection of apoptosis induced by EAPB0203, which constitutes a direct demonstration of the involvement of caspases in cell death and the inhibition of growth induced by EAPB0203.

Activation of the mitochondrial route is controlled by members of the Bcl-2 family. EAPB0203 induced a significant reduction in the expression of IAP-1 proteins (caspase inhibitors) and bcl-xL (anti-apoptotic protein). In the cell lines infected or not infected by HTLV-I, the effect of EAPB0203 on regulators of the cell cycle is studied. A significant increase in the expression of proteins p21 and p53 is observed in HuT-102 and MT2 cells (HTLV-I-positive) treated with EAPB0203.

These results suggest that p53 plays an important role in the termination of the cell cycle in $G_2$. Indeed, p53 positively regulates the transcription of p21. Activation of p21 by p53 causes a reduction in expression of B and Cdc2 cyclins and thereafter the termination of the cell cycle in G2/M.

The involvement of apoptosis after treatment by EAPB0203 is demonstrated. Indeed, activation of the intrinsic mitochondrial route in the cells studied is shown. The drop in the mitochondrial transmembrane potential obtained after treatment supports a pro-apoptotic process enabling opening of the mitochondrial pores and thus the release of apoptogenic molecules such as the cytochrome C.

The study of the effect of EAPB0203 on cellular proliferation and apoptosis of transformed malignant T-cells and HTLV-I-negative cells shows selective effects on malignant cells, and supports a therapeutic role for EAPB0203 among patients with ATL and other HTLV-I-negative lymphomas, as a systemic or topical therapy for cutaneous lymphomas.

The invention claimed is:
1. The compound of formula (V):

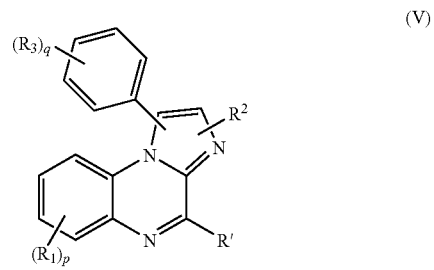

(V)

wherein $R_1$, $R_2$, and $R_3$ represent independently an atom of hydrogen, a halogen or a group chosen among hydroxy, $C_1$-$C_4$ alkyl, $C_1$-$C_4$ alkoxy, amino, $C_1$-$C_4$ alkylamino, $C_1$-$C_4$ dialkylamino, cyano, —$CF_3$, —$(CH_2)_n NR_4 R_5$, or —NH—$(CH_2)_n NR_4 R_5$ radicals, R' is selected from methylamino, dimethylamino, ethylamino, diethylamino, aminomethylamine or aminoethylamine group, n is 1,2,3 or 4, p is 1,2,3 or 4, q is 1,2,3,4 or 5, $R_4$ and $R_5$ represent independently an atom of hydrogen or group chosen among the linear or branched $C_1$-$C_4$ alkyl and/or a physiologically acceptable salt thereof.

2. The compound according to claim 1 wherein $R_1$, $R_2$ and $R_3$ represent independently an atom of hydrogen, a halogen or a group chosen among the groups methyl, ethyl, propyl, isopropyl, butyl, isobutyl, and tert-butyl.

3. The compound according to claim 1 wherein $R_3$ is selected among H, Cl, Br, F, hydroxy, methyl, methoxy, ethoxy, —$CF_3$, and CN.

4. The compound according to claim 1 wherein $R_3$ is selected among H, hydroxy, methoxy, ethoxy, Br, $CF_3$, and Cl.

5. The compound according to claim 1 wherein q is 1.

6. The compound according to claim 1 wherein R' is —NH—$CH_3$, or —NH—$(CH_2)_2$—$NH_2$.

7. The compound of claim 1, wherein $R_1$ is H; $R_2$ is H, $R_3$ is —$OCH_3$, and R' is $NHCH_3$.

8. The compound of formula (VIII):

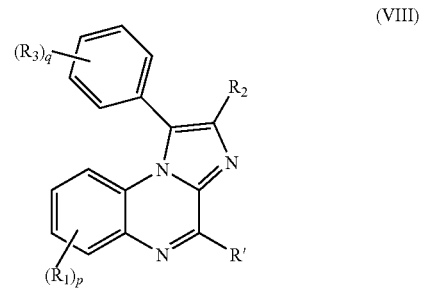

(VIII)

wherein $R_1$, $R_2$, and $R_3$ represent independently an atom of hydrogen, a halogen or a group chosen among hydroxy, $C_1$-$C_4$ alkyl, $C_1$-$C_4$ alkoxy, amino, $C_1$-$C_4$ alkylamino, $C_1$-$C_4$ dialkylamino, cyano, —$CF_3$, —$(CH_2)$—$NR_4 R_5$, or —NH—$(CH_2)_n NR_4 R_5$ radicals, R' represents independently an atom of hydrogen, a halogen or a group chosen among $C_1$-$C_4$ alkyl, $C_1$-$C_4$ alkoxy, amino, $C_1$-$C_4$ alkylamino, $C_1$-$C_4$ dialkylamino, cyano, —$CF_3$, —$(CH_2)_n NR_4 R_5$, —$(CH_2)_n COR_4$, or —NH—$(CH_2)_n NR_4 R_5$ radicals, n is 0,1,2,3 or 4,
p is 1,2,3, or 4,
q is 1,2,3 or 5,
$R_4$ and $R_5$ represent independently an atom of hydrogen or group chosen among the linear or branched $C_1$-$C_4$ alkyl
and/or a physiologically acceptable salt thereof.

9. The compound according to claim 8 of formula (IX):

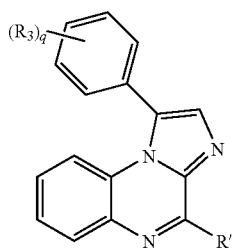

(IX)

and/or a physiologically acceptable salt thereof.

10. A compound selected from the group consisting of:
N-methyl-1-phenylimidazo[1,2-a]quinoxalin-4-amine,
N-methyl-1-(2-hydroxyphenyl)imidazo[1,2-a]quinoxalin-4-amine,
N-methyl-1-(3-hydroxyphenyl)imidazo[1,2-a]quinoxalin-4-amine,
N-methyl-1-(4-hydroxyphenyl)imidazo[1,2-a]quinoxalin-4-amine,
N-methyl-1-(2,4-dihydroxyphenyl)imidazo[1,2-a]quinoxalin-4-amine,
N-methyl-1-(2,3-dihydroxyphenyl)imidazo[1,2-a]quinoxalin-4-amine,
N-methyl-1-(2-methoxyphenyl)imidazo[1,2-a]quinoxalin-4-amine,
N-methyl-1-(3-methoxyphenyl)imidazo[1,2-a]quinoxalin-4-amine,
N-methyl-1-(4-methoxyphenyl)imidazo[1,2-a]quinoxalin-4-amine,
N-methyl-1-(2,4-dimethoxyphenyl)imidazo[1,2-a]quinoxalin-4-amine,
N-methyl-1-(2,3-dimethoxyphenyl)imidazo[1,2-a]quinoxalin-4-amine,
N-methyl-1-(3-ethoxyphenyl)imidazo[1,2-a]quinoxalin-4-amine,
N-methyl-1-(4-ethoxyphenyl)imidazo[1,2-a]quinoxalin-4-amine,
N-methyl-1-(3-bromophenyl)imidazo[1,2-a]quinoxalin-4-amine,
N-methyl-1-(4-bromophenyl)imidazo[1,2-a]quinoxalin-4-amine,
N-methyl-1-(3-(trifluoromethyl)phenyl))imidazo[1,2-a]quinoxalin-4-amine,
N-methyl-1-(4-(trifluoromethyl)phenyl))imidazo [1,2-a]quinoxalin-4-amine,
N-methyl-1-(3-chlorophenyl)imidazo [1,2-a]quinoxalin-4-amine,
N-methyl-1-(4-chlorophenyl)imidazo [1,2-a]quinoxalin-4-amine,
N-methyl1-(3-fluorophenyl)imidazo [1,2-a]quinoxalin-4-amine,
N-methyl1-(4-fluorophenyl)imidazo [1,2-a]quinoxalin-4-amine,
N-methyl1-(3-cyanophenyl)imidazo [1,2-a]quinoxalin-4-amine,
N-methyl1-(4-cyanophenyl)imidazo [1,2-a]quinoxalin-4-amine,
N-(2-aminoethyl)-1-(2-hydroxyphenyl)imidazo [1,2-a]quinoxalin-4-amine,
N-(2-aminoethyl)-1-(3-hydroxyphenyl)imidazo [1,2-a]quinoxalin-4-amine,
N-(2-aminoethyl)-1-(4-hydroxyphenyl)imidazo [1,2-a]quinoxalin-4-amine,
N-(2-aminoethyl)-1-(2,4-dihydroxyphenyl)imidazo [1,2-a]quinoxalin-4-amine,
N-(2-aminoethyl)-1-(2,3-dihydroxyphenyl)imidazo [1,2-a]quinoxalin-4-amine,
N-(2-aminoethyl)-1-(2-methoxyphenyl)imidazo [1,2-a]quinoxalin-4-amine,
N-(2-aminoethyl)-1-(3-methoxyphenyl)imidazo [1,2-a]quinoxalin-4-amine,
N-(2-aminoethyl)1-(4-methoxyphenyl)imidazo [1,2-a]quinoxalin-4-amine,
N-(2-aminoethyl)1-(2,4-dimethoxyphenyl)imidazo [1,2-a]quinoxalin-4-amine,
N-(2-aminoethyl)1-(2,3-dimethoxyphenyl)imidazo [1,2-a]quinoxalin-4-amine,
N-(2-aminoethyl)1-(3-ethoxyphenyl)imidazo [1,2-a]quinoxalin-4-amine,
N-(2-aminoethyl)1-(4-ethoxyphenyl)imidazo [1,2-a]quinoxalin-4-amine,
N-(2-aminoethyl)1-(3-bromophenyl)imidazo [1,2-a]quinoxalin-4-amine,
N-(2-aminoethyl)1-(4-bromophenyl)imidazo [1,2-a]quinoxalin-4-amine,
N-(2-aminoethyl)-1-(3-(trifluoromethyl)phenyWimidazo [1,2-a]quinoxalin-4-amine,
N-(2-aminoethyl)-1-(4-(trifluoromethyl)phenyWimidazo [1,2-a]quinoxalin-4-amine,
N-(2-aminoethyl)-1-(3-chlorophenyl)imidazo [1,2-a]quinoxalin-4-amine,
N-(2-aminoethyl)-1-(4-chlorophenyl)imidazo [1,2-a]quinoxalin-4-amine,
N-(2-aminoethyl)-1-(3-fluorophenyl)imidazo [1,2-a]quinoxalin-4-amine,
N-(2-aminoethyl)-1-(4-fluorophenyl)imidazo [1,2-a]quinoxalin-4-amine,
N-(2-aminoethyl)-1-(3-cyanophenyl)imidazo [1,2-a]quinoxalin-4-amine,
N-(2-aminoethyl)-1-(4-cyanophenyl)imidazo [1,2-a]quinoxalin-4-amine,
1-phenylimidazo [1,2-a]quinoxalin-4-amine,
1-(2-hydroxyphenyl)imidazo [1,2-a]quinoxaline,
1-(3-hydroxyphenyl)imidazo [1,2-a]quinoxaline,
1-(4-hydroxyphenyl)imidazo [1,2-a]quinoxaline,
1-(2,4-dihydroxyphenyl)imidazo [1,2-a]quinoxalin-4-amine,
1-(2,3-dihydroxyphenyl)imidazo [1,2-a]quinoxalin-4-amine,
1-(2-methoxyphenyl)imidazo[1,2-a]quinoxalin-4-amine,
1-(3-methoxyphenyl)imidazo[1,2-a]quinoxalin-4-amine,
1-(4-methoxyphenyl)imidazo[1,2-a]quinoxalin-4-amine,
1-(2,4-dimethoxyphenyl)imidazo[1,2-a]quinoxalin-4-amine,
1-(2,3-dimethoxyphenyl)imidazo[1,2-a]quinoxalin-4-amine,
1-(3-ethoxyphenyl)imidazo[1,2-a]quinoxalin-4-amine,
1-(4-ethoxyphenyl)imidazo[1,2-a]quinoxalin-4-amine, 1-(3-bromophenyl)imidazo[1,2-a]quinoxalin-4-amine,
1-(4-bromophenyl)imidazo[1,2-a]quinoxalin-4-amine,
1-(3-(trifluoromethyl)phenyl))imidazo[1,2-a]quinoxalin-4-amine,
1-(4-(trifluoromethyl)phenyl))imidazo[1,2-a]quinoxalin-4-amine,
1-(3-chlorophenyl)imidazo[1,2-a]quinoxalin-4-amine,
1-(4-chlorophenyl)imidazo[1,2-a]quinoxalin-4-amine,
1-(3-fluorophenyl)imidazo[1,2-a]quinoxalin-4-amine,
1-(4-fluorophenyl)imidazo[1,2-a]quinoxalin-4-amine,
1-(3-cyanophenyl)imidazo[1,2-a]quinoxalin-4-amine,
1-(4-cyanophenyl)imidazo[1,2-a]quinoxalin-4-amine,
4-Chloro-1-phenylimidazo[1,2-a]quinoxaline,
4-Chloro-1-(2-hydroxyphenyl)imidazo[1,2-a]quinoxaline,
4-Chloro-1-(3-hydroxyphenyl)imidazo[1,2-a]quinoxaline,
4-Chloro-1-(4-hydroxyphenyl)imidazo[1,2-a]quinoxaline,
4-Chloro-1-(2-methoxyphenyl)imidazo[1,2-a]quinoxaline,
4-Chloro-1-(3-methoxyphenyl)imidazo[1,2-a]quinoxaline,
4-Chloro-1-(4-methoxyphenyl)imidazo[1,2-a]quinoxaline,
4-Chloro-1-(2,4-dimethoxyphenyl)imidazo[1,2-a]quinoxaline,
4-Chloro-1-(2,3-dimethoxyphenyl)imidazo[1,2-a]quinoxaline,
4-methoxy-1-phenylimidazo[1,2-a]quinoxaline,
4-methoxy-1-(2-hydroxyphenyl)imidazo[1,2-a]quinoxaline,
4-methoxy-1-(3-hydroxyphenyl)imidazo[1,2-a]quinoxaline,
4-methoxy-1-(4-hydroxyphenyl)imidazo[1,2-a]quinoxaline,
4-methoxy-1-(2-methoxyphenyl)imidazo[1,2-a]quinoxaline,
4-methoxy-1-(3-methoxyphenyl)imidazo[1,2-a]quinoxaline,
4-methoxy-1-(4-methoxyphenyl)imidazo[1,2-a]quinoxaline,
4-methoxy-1-(2,-dimethoxyphenyl)imidazo[1,2-a]quinoxaline, and
4-methoxy-1-(2,3-dimethoxyphenyl)imidazo[1,2-a]quinoxaline
and physiologically acceptable salts thereof.

* * * * *